US010281463B2

(12) United States Patent
Segal et al.

(10) Patent No.: US 10,281,463 B2
(45) Date of Patent: May 7, 2019

(54) METHODS OF DETERMINING CELLULAR PHENOTYPES

(71) Applicant: Technion Research & Development Foundation Limited, Haifa (IL)

(72) Inventors: Ester Segal, Haifa (IL); Nadav Ben-Dov, Moshav Ein-Ayala (IL)

(73) Assignee: TECHNION RESEARCH & DEVELOPMENT FOUNDATION LIMITED, Haifa (IL)

( * ) Notice: Subject to any disclaimer, the term of this patent is extended or adjusted under 35 U.S.C. 154(b) by 0 days.

(21) Appl. No.: 15/556,330

(22) PCT Filed: Mar. 9, 2016

(86) PCT No.: PCT/IB2016/051333
§ 371 (c)(1),
(2) Date: Sep. 7, 2017

(87) PCT Pub. No.: WO2016/142878
PCT Pub. Date: Sep. 15, 2016

(65) Prior Publication Data
US 2018/0067111 A1    Mar. 8, 2018

Related U.S. Application Data

(60) Provisional application No. 62/130,259, filed on Mar. 9, 2015.

(51) Int. Cl.
G01J 3/28 (2006.01)
G01N 33/543 (2006.01)
G01N 21/47 (2006.01)
G01D 5/26 (2006.01)
(Continued)

(52) U.S. Cl.
CPC ....... G01N 33/54373 (2013.01); G01D 5/266 (2013.01); G01N 21/4788 (2013.01);
(Continued)

(58) Field of Classification Search
CPC ....... G01N 33/54373; G01N 33/48735; G01N 33/5302; G01N 33/50; G01N 21/4788;
(Continued)

(56) References Cited

U.S. PATENT DOCUMENTS

| 5,738,825 A * | 4/1998 | Rudigier ............... B01L 3/5085 |
| | | 422/425 |
| 8,349,617 B2 * | 1/2013 | Weiss ....................... B41D 7/00 |
| | | 422/82.05 |
| 2007/0172894 A1 * | 7/2007 | Genick ................. B01L 3/5085 |
| | | 435/7.2 |

FOREIGN PATENT DOCUMENTS

| WO | WO 2014/155381 | 10/2014 |
| WO | WO 2016/142878 | 9/2016 |

OTHER PUBLICATIONS

International Search Report and the Written Opinion Dated May 9, 2016 From the International Searching Authority Re. Application No. PCT/IB2016/051333. (11 Pages).
(Continued)

*Primary Examiner* — Tarifur R Chowdhury
*Assistant Examiner* — Jonathon Cook
(74) *Attorney, Agent, or Firm* — The Roy Gross Law Firm, LLC; Roy Gross

(57) ABSTRACT

Methods of determining a phenotype of cells in a biological sample are provided. The methods are based measuring a refractive index of said cells based on a diffraction pattern received from a diffraction grating having a plurality of compartments having lateral dimensions such that said cells can fit therein.

20 Claims, 23 Drawing Sheets
(23 of 23 Drawing Sheet(s) Filed in Color)

(51) Int. Cl.
*G01N 21/85* (2006.01)
*G01N 33/487* (2006.01)
*G01N 33/53* (2006.01)

(52) U.S. Cl.
CPC ....... *G01N 21/85* (2013.01); *G01N 33/48735* (2013.01); *G01N 33/5302* (2013.01)

(58) Field of Classification Search
CPC .. G01N 21/85; G01N 21/552; G01N 21/8483; G01N 2021/211; G01N 2021/212; G01J 3/2803; G01J 3/18; G01J 3/02; G01B 11/303; G01B 11/06
USPC .................. 356/326, 328, 445, 446
See application file for complete search history.

(56) References Cited

OTHER PUBLICATIONS

Massad-Ivanir et al. "Trap and Track: Designing Self-Reporting Porous Si Photonic Crystals for Rapid Bacteria Detection", The Analyst, XP055268942, 139(16): 3885-3894, Aug. 21, 2014. Abstract, P.3886, Section 2.2, Section 3 on P.3887-3891.

Mirsky et al. "Optical Biosensing of Bacteria and Cells Using Porous silicon Based, Photonic Lamellar Gratings", Applied Physics Letters, XP055268972, 103(3): 033702-1-033702-4, Jul. 15, 2013. Abstract, P.033702-3, 1-h Col., First Full Para—P.033702-4, 1-h Col., First Full Para.

Schwartz et al. "The Smart Petri Dish: A Nonstructured Photonic Crystal for Real-Time Monitoring of Living Cells", Langmuir, XP055268976, 22(16): 7084-7090, Published on Web May 19, 2006.

Tang et al. "Rapid antibiotic Susceptibility Testing in A Microfluidic pH Sensor", Analytical Chemistry, XP055268974, 85(5): 2787-2794, Jan. 29, 2013. Abstract, P.2789, r-h Col., 2n-3rd Para, Fig. 1.

International Preliminary Report on Patentability dated Sep. 21, 2017 From the International Bureau of WIPO Re. Application No. PCT/IB2016/051333. (9 Pages).

Communication Pursuant to Article 94(3) EPC dated Aug. 23, 2018 From the European Patent Office Re. Application No. 16712076.5. (6 Pages).

* cited by examiner

METHODS OF DETERMINING CELLULAR PHENOTYPES

RELATED APPLICATION

This application is a National Phase of PCT Patent Application No. PCT/IB2016/051333 having International filing date Mar. 9, 2016, which claims the benefit of priority under 35 USC § 119(e) of U.S. Provisional Patent Application No. 62/130,259 filed on Mar. 9, 2015. The contents of the above applications are all incorporated by reference as if fully set forth herein in their entirety.

FIELD AND BACKGROUND OF THE INVENTION

Biosensing is an important field in industry, and especially in the food industry, where the detection and monitoring of the levels of bio-contaminants, such as bacterial levels in food products, is of critical importance in maintaining modern health standards. In the food industry, the need for constant monitoring of products coming off production lines is particularly important and problematic, since any production fault resulting in bio-contamination of the products must be detected before products are shipped for marketing. This is currently often done by means of testing cultures grown from samples from each production line and batch. However, because of the time taken to grow and tests such cultures, even using modern accelerated culture growth and measurement techniques, a large number of products may have been produced and packed ready for shipping before the contamination is detected, thus leading to considerable loss. There exist technologies, such as surface plasma resonance (SPR) for instance, which enable constant monitoring of the bio-contaminant levels in products, but such technologies are costly—a typical installation costing many tens of thousands of dollars. Because of the large number of different products produced on different production lines, such bio-sensing technologies are often prohibitively expensive for general use in the food industry, and there appear to exist no low cost biosensing equipment which can perform cost effective widespread online monitoring of food products.

In recent years, porous Si (hereinafter PSi) has emerged as a promising nanomaterial for biosensing applications, and for sensing other targets with nanoscale dimensions. Common PSi-based optical sensors and biosensors consist of thin films of either nano-pores (typically of dimensions less than 20 nm) or meso-pores (typically in the range of 20-100 nm) which thus have cross sectional dimensions much smaller than the optical wavelengths used. The pores are generally randomly generated during production of the thin film device. The operation of these sensors is based on replacing the media in the pores and/or infiltrating with the target analyte, and observing the resulting changes of optical reflectivity. A change in the effective refractive index of the PSi film is manifested as a wavelength shift in the reflectivity spectrum. Only target molecules which penetrate into these nano structures, can be detected. Indeed, sensing and biosensing of various chemical and biological analytes, such as fluorescent molecules, organophosphates, volatile organic compounds, DNA, and proteins have been successfully demonstrated. Many of these studies employ the method of reflective interferometric Fourier transform spectroscopy (RIFTS) to monitor biological interaction within mesoporous Si thin films.

Such filled or partially filled, randomly located pores can be viewed as simply having a different effective refractive index from that of unfilled pores, because the pores are much smaller than the optical wavelength. Consequently, the random nature of the pores does not result in scatter of the light, but rather in an averaging out of the overall reflected light from the combination of the silicon substrate and the pores, both filled and unfilled. However, this detection scheme is not applicable for targeting large biological or other species, such as those ranging in size of from approximately a few hundreds of nanometers up to several microns and more, including cells, bacteria and viruses. If porous silicon is produced having such larger pores, the substrate becomes a material known as "black silicon", which appears as such because it strongly scatters light from the random distribution of the large sized pores. Essentially all of the incident light is randomly scattered by the pores and is absorbed in the medium, such that it cannot be used for sensing. Therefore, the conventional porous silicon technology cannot be used for sensing or bio-sensing of larger targets of sizes which are a significant fraction of the wavelength of the light used for the sensing.

There exist alternative methods which monitor changes in the intensity of the reflectivity spectrum upon direct capture of larger cellular targets on top of the biosensor surface, rather than in the pores thereof. However, these types of sensors are limited, since intensity changes of the reflectivity spectrum may arise from unpredictable sources, such as environmental effects and non-specific binding events. In addition, the sensitivity may be low because such surface-binding sensors do not take advantage of the large porous volume.

In recent years attempts have been made to develop new bioassays and biosensors for the rapid detection of bacteria in general, and pathogenic bacteria in particular. However, despite the significant progress in the field, current technologies lack the ability to detect microorganisms in "real time" or outside the laboratory environment WO 2014/155381 teaches a method and apparatus for bacterial monitoring.

SUMMARY OF THE INVENTION

According to an aspect of some embodiments of the present invention there is provided a method of determining a phenotype of cells in a biological sample, the method comprising:

(a) incubating for a predetermined time the biological sample comprising the cells on a diffraction grating containing an ordered array of compartments having lateral dimensions such that the cells can fit therein;

(b) continuously detecting over the predetermined time illumination diffracted from the diffraction grating comprising the cells upon illumination of the surface with illumination over a range of wavelengths and generating therefrom an output spectrum signal;

(c) determining from the output spectrum signal a time-dependence change of an effective optical thickness (EOT) of the compartments incubated with the biological sample, the time-dependence being indicative of the phenotype of the cells in the biological sample.

According to an aspect of some embodiments of the present invention there is provided a method of determining a phenotype of cells, the method comprising:

(a) placing the cells in a plurality of compartments of a diffraction grating;

(b) diffracting a polychromatic light beam by the diffraction grating;

(c) calculating a parameter indicative of a refractive index of the cells based on a diffraction pattern received from the diffraction grating; and (d) determining a time-dependence of a change of the parameter, the time-dependence being indicative of the phenotype of the cells in the biological sample.

According to some embodiments of the invention, the parameter comprises effective optical thickness (EOT) of the compartments, and the change is with respect to a value of the EOT in the absence of the cells.

According to some embodiments of the invention, the diffracting comprises effecting reflective diffraction.

According to some embodiments of the invention, the diffracting comprises effecting transmissive diffraction.

According to some embodiments of the invention, the polychromatic light beam is generally white.

According to some embodiments of the invention, the biological sample comprises a test agent.

According to some embodiments of the invention, the diffraction grating comprises a test agent adhered to the compartments.

According to some embodiments of the invention, the method further comprises performing the method in an absence of the test agent.

According to some embodiments of the invention, the change of the parameter is a change of a value the parameter in the presence of the test agent relative to a value of a value the parameter in the absence of the test agent.

According to some embodiments of the invention, the time-dependence is indicative of an effect of the test agent on the phenotype of the cells in the biological sample.

According to some embodiments of the invention, the phenotype is selected from the group consisting of viability, motility, biofilm production, colonization, protein production and lipid production.

According to some embodiments of the invention, the test agent is a cytostatic agent.

According to some embodiments of the invention, the test agent is a cytocidal agent.

According to some embodiments of the invention, when the time-dependence is indicative of a decrease in an effective optical thickness (EOT), the test agent is a cytocidal agent.

According to some embodiments of the invention, when the time-dependence is substantially flat the test agent is a cytostatic agent.

According to some embodiments of the invention, the cells are incubated with the diffraction grating so as to fill the compartments prior to adding the test agent.

According to some embodiments of the invention, the phenotype is viability.

According to some embodiments of the invention, the phenotype is motility.

According to some embodiments of the invention, the cells are bacteria.

According to some embodiments of the invention, the cells are eukaryotic cells.

According to some embodiments of the invention, the eukaryotic cells are cancer cells.

According to some embodiments of the invention, the test agent is selected from the group consisting of an antibiotic, a chemotherapy, a radioisotope, a herbicide and a fungicide.

According to an aspect of some embodiments of the present invention there is provided a computer software product. The computer software product comprises a computer-readable medium in which program instructions are stored, which instructions, when read by a data processor, cause the data processor to receive data pertaining to a diffraction pattern of light diffracted off a diffraction grating having a plurality of compartments containing cells, to calculates a parameter indicative of a refractive index of the cells based on the diffraction pattern, and to determine a time-dependence of a change of the parameter, the time-dependence being indicative of the phenotype of the cells in the biological sample.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

Implementation of the method and/or system of embodiments of the invention can involve performing or completing selected tasks manually, automatically, or a combination thereof. Moreover, according to actual instrumentation and equipment of embodiments of the method and/or system of the invention, several selected tasks could be implemented by hardware, by software or by firmware or by a combination thereof using an operating system.

For example, hardware for performing selected tasks according to embodiments of the invention could be implemented as a chip or a circuit. As software, selected tasks according to embodiments of the invention could be implemented as a plurality of software instructions being executed by a computer using any suitable operating system. In an exemplary embodiment of the invention, one or more tasks according to exemplary embodiments of method and/or system as described herein are performed by a data processor, such as a computing platform for executing a plurality of instructions. Optionally, the data processor includes a volatile memory for storing instructions and/or data and/or a non-volatile storage, for example, a magnetic hard-disk and/or removable media, for storing instructions and/or data. Optionally, a network connection is provided as well. A display and/or a user input device such as a keyboard or mouse are optionally provided as well.

BRIEF DESCRIPTION OF SEVERAL VIEWS OF THE DRAWINGS

The patent or application file contains at least one drawing executed in color. Copies of this patent or patent application publication with color drawing(s) will be provided by the Office upon request and payment of the necessary fee.

Some embodiments of the invention are herein described, by way of example only, with reference to the accompanying drawings and images. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIGS. 1A-F show a top view of a 2D pillar periodic array with proliferating bacterial cells (FIG. 1A), light reflected from the pores top and bottom creates a phase delay between the incident and the reflected beams (FIG. 1B), an interference spectrum associated with the pores periodicity (FIG. 1C), Fast Fourier Transform (FFT) of the raw spectrum (FIG. 1D), an illustration demonstrating the effect of the presence of bacterial cells presence within the pores on the refractive index of the porous layer, and a graph demonstrating that the bacteria fraction in the pores can be monitored by collecting the effective optical thickness (EOT).

Figure 2:
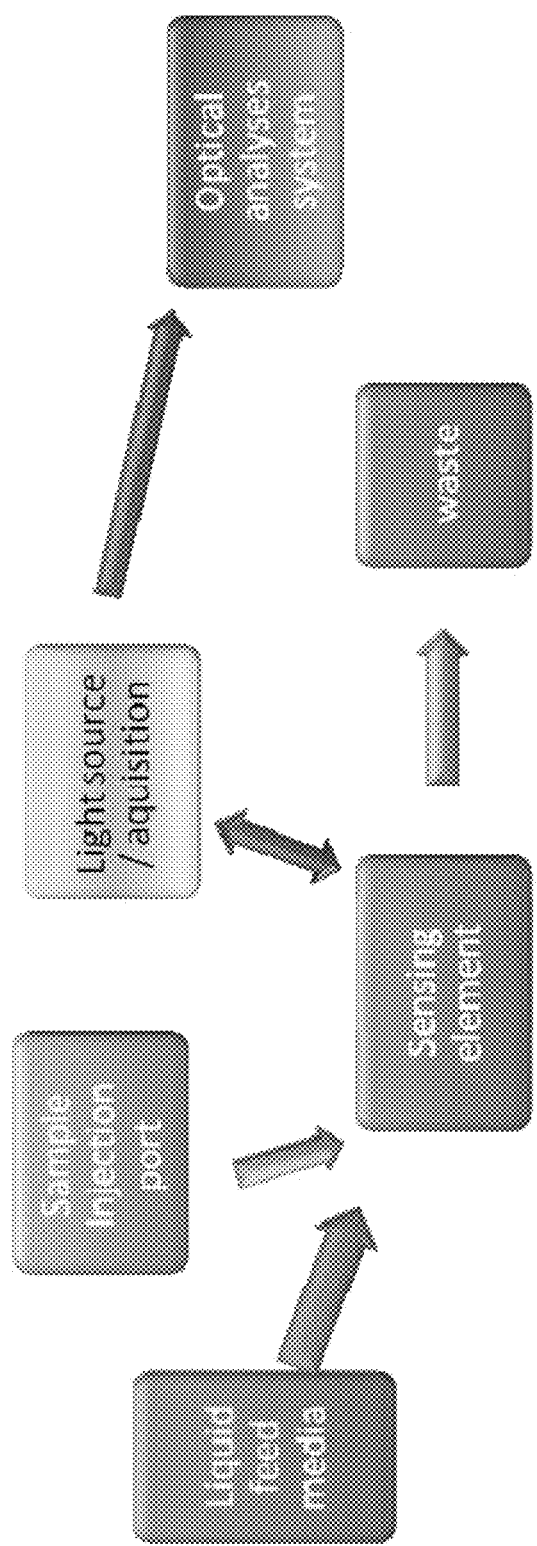

FIG. 2 is a flowchart diagram illustrating a method suitable for monitoring of the light interferometry spectra obtained from a surface with reflective periodic topography (PRT), prior, during and/or following the controlled introduction of bacterial suspensions to it and/or addition of drugs/substances.

Figure 3:
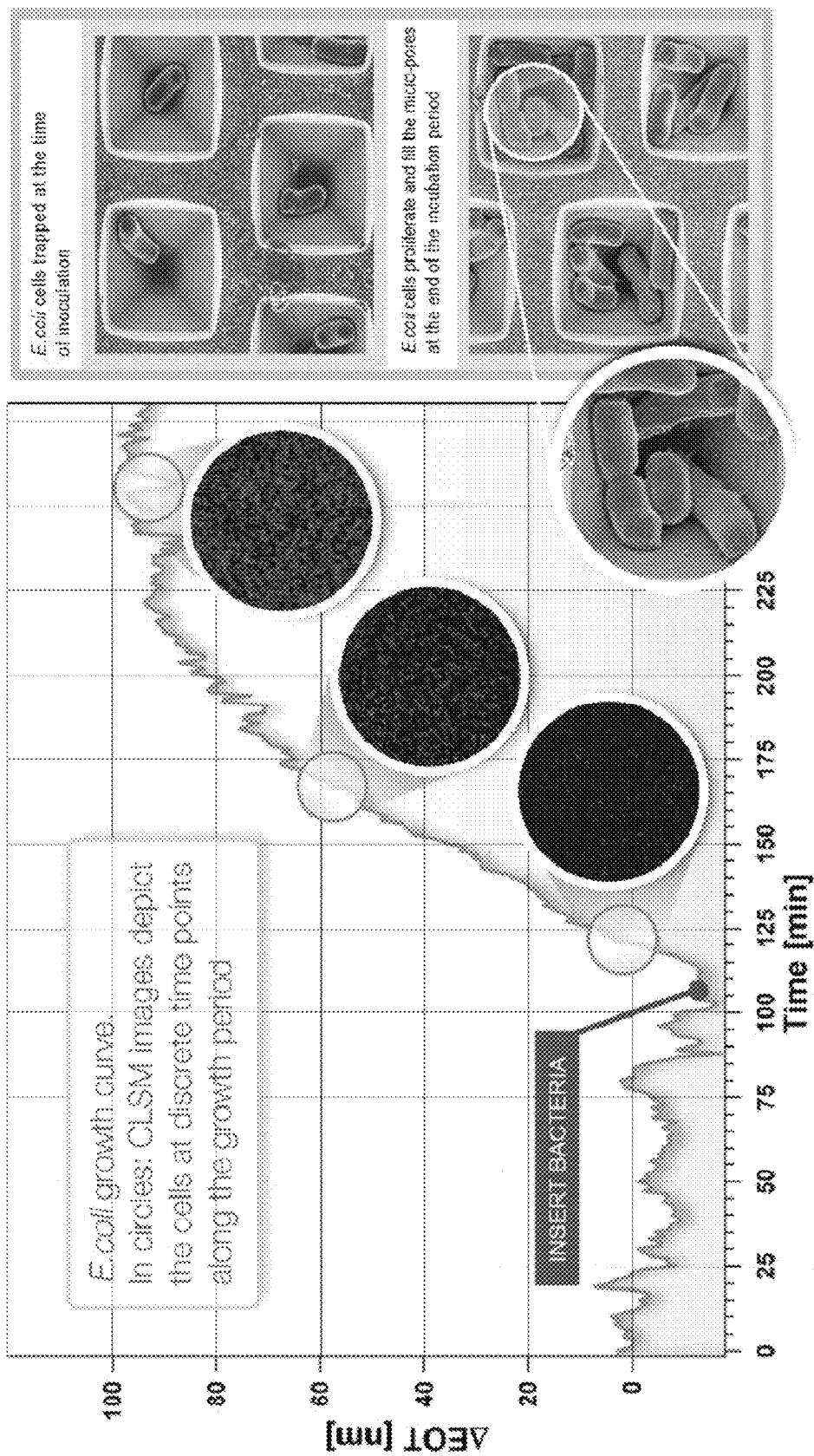

FIG. 3 describes a procedure in which a finite number of cells is placed on a photonic microarrays diffraction grating. The shift in EOT relates to the growing number of cells in the diffraction grating that result from cell proliferation.

Figure 4:
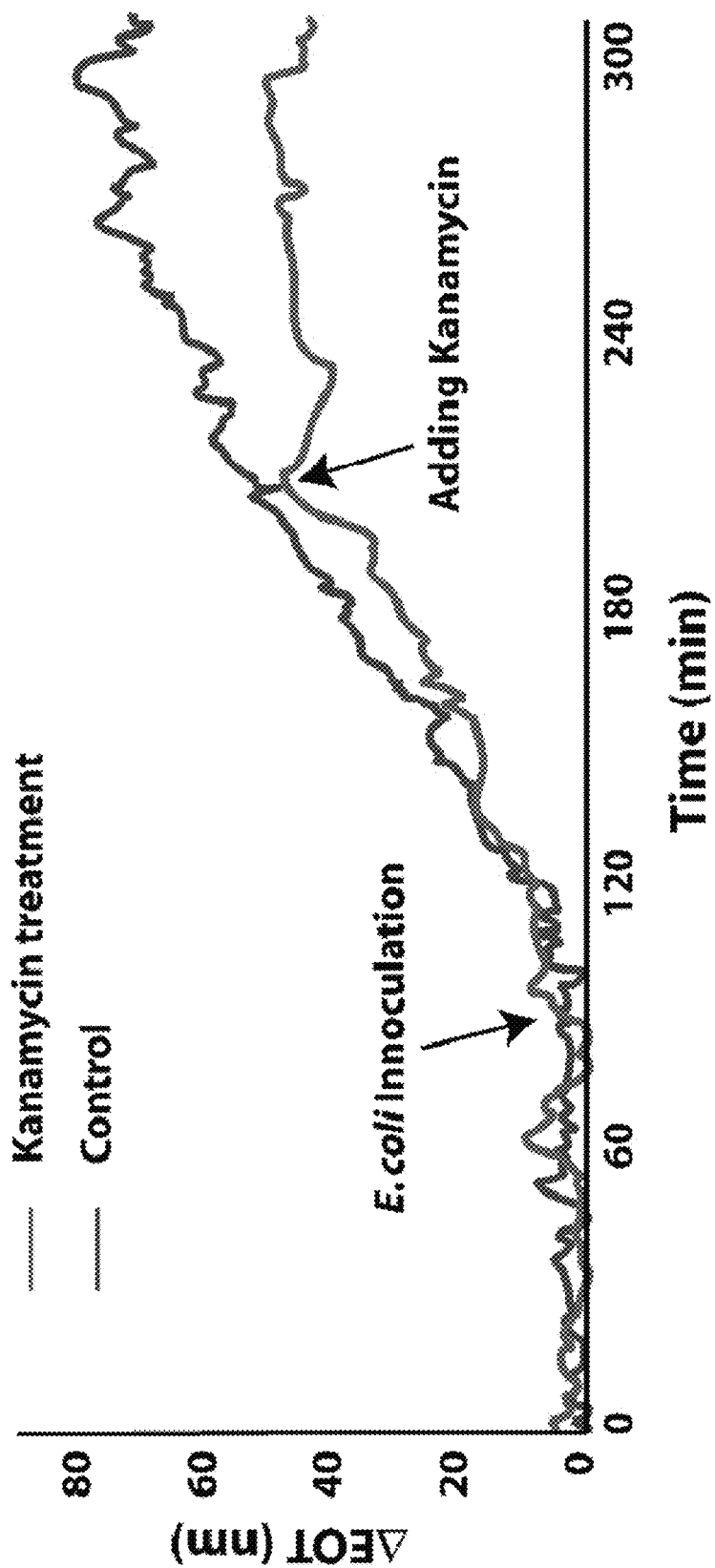

FIG. 4 demonstrates that the addition of an antibiotic substance that restricts cell growth can be traced through the induced change in the rate of EOT shift, with proportionality to the concentration of the substance. The MIC (minimal inhibitory concentration) can be determined when the rate of EOT shift becomes insignificant.

Figure 5A:
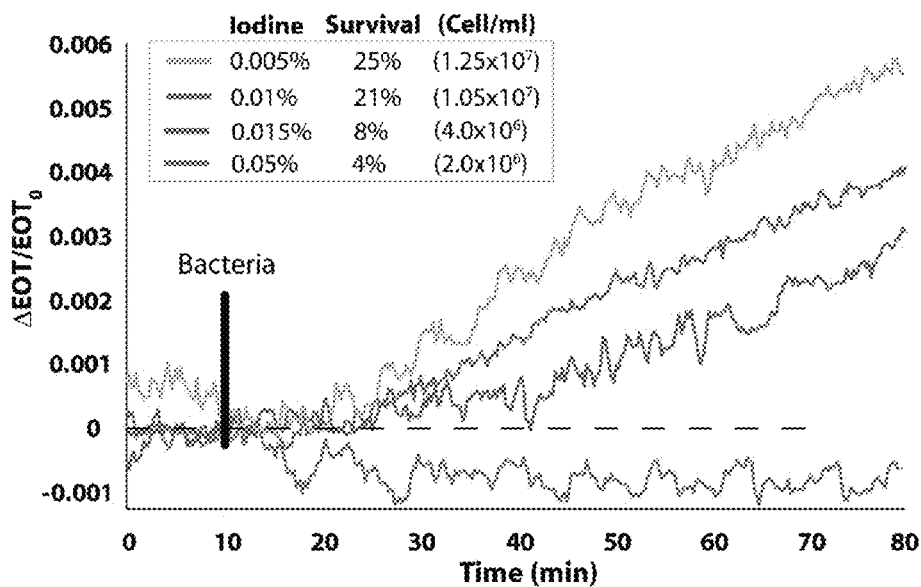
Figure 5B:
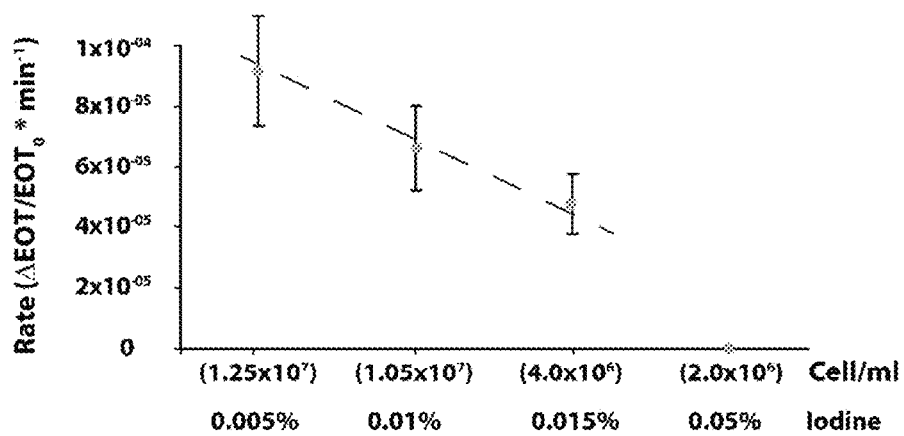

FIGS. 5A and 5B show that the presence of bactericidal molecules in the bacterial suspension can be traced through the induced change in the rate of EOT shift, with proportionality to the concentration of said substance.

Figure 5C:
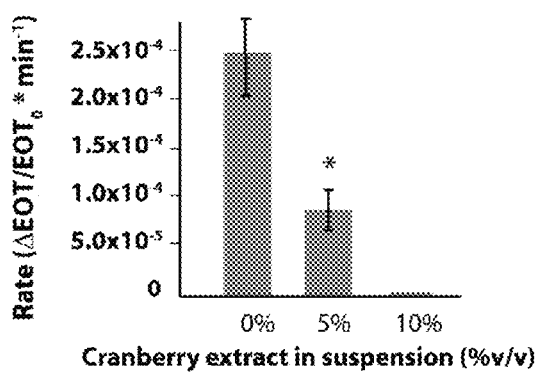

FIG. 5C shows that the presence of an anti-attachment factor in the bacterial suspension can be traced through the induced change in the rate of EOT shift, with proportionality to the concentration of said substance.

Figure 6A:
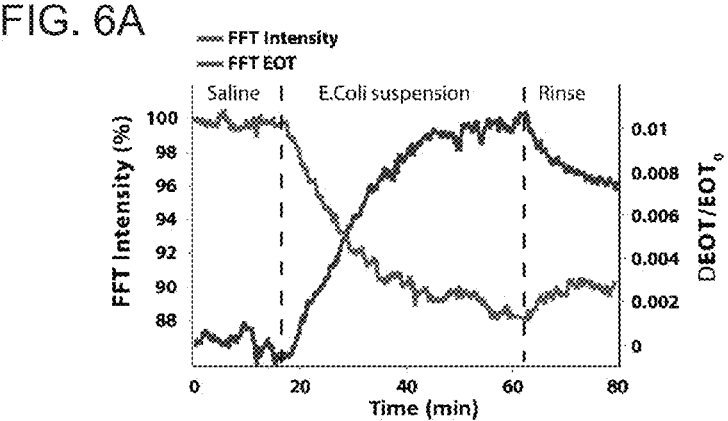

FIGS. 6A to 6F3 demonstrates cell adherence stability at the pores.

Figure 7:
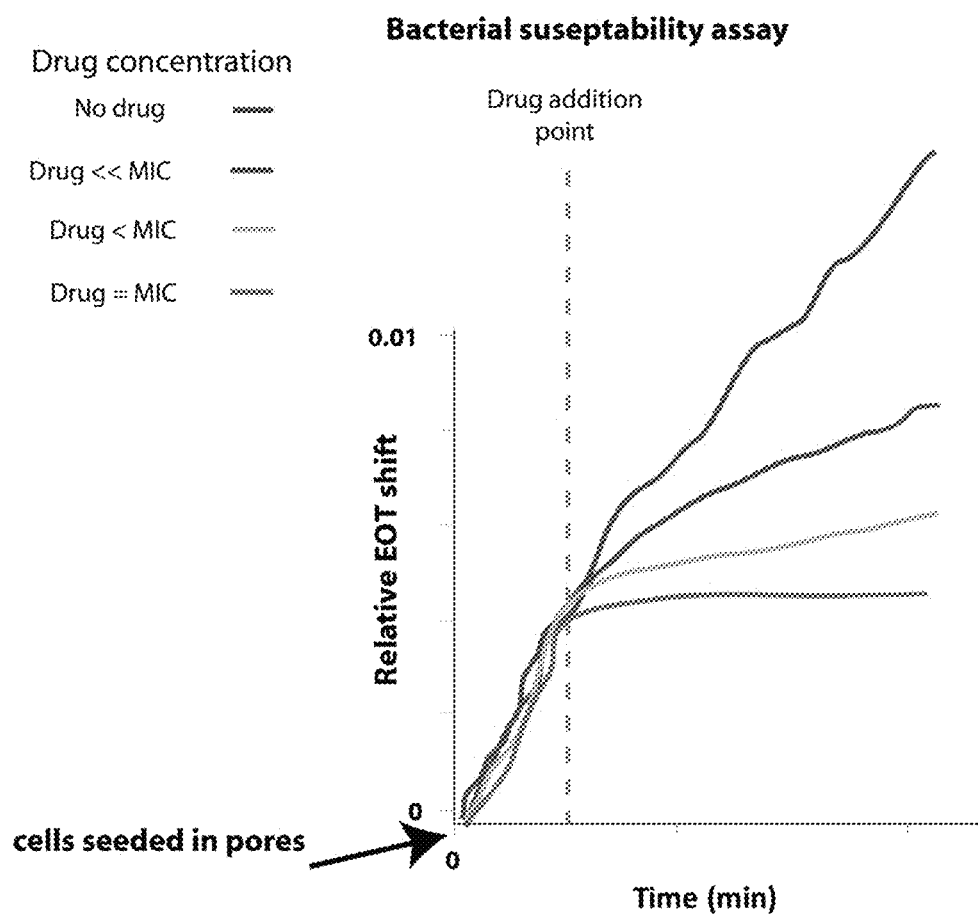

FIG. 7 is a graph showing results of a bacterial susceptibility assay. Shown is a relative EPT shift as a function of the time.

Figure 8:
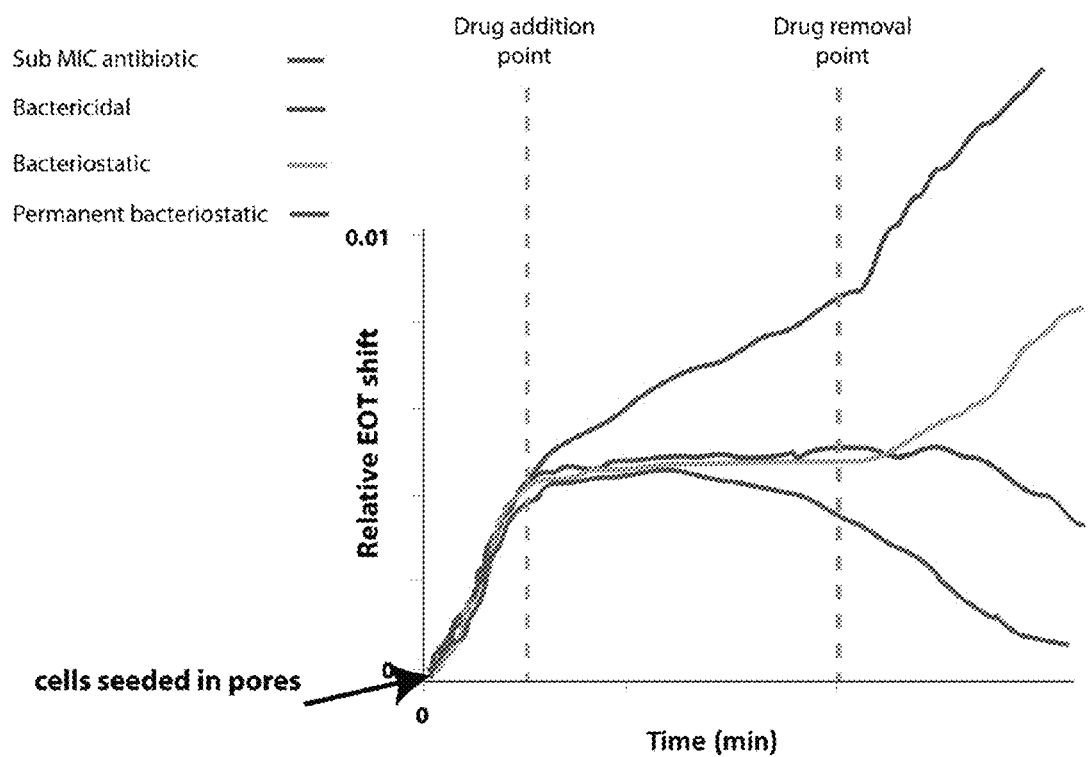

FIG. 8 is a graph showing results of an experiment in which bacterial kinetic reaction to different mechanism of drugs was monitored. Shown is a relative EPT shift as a function of the time.

Figure 9:
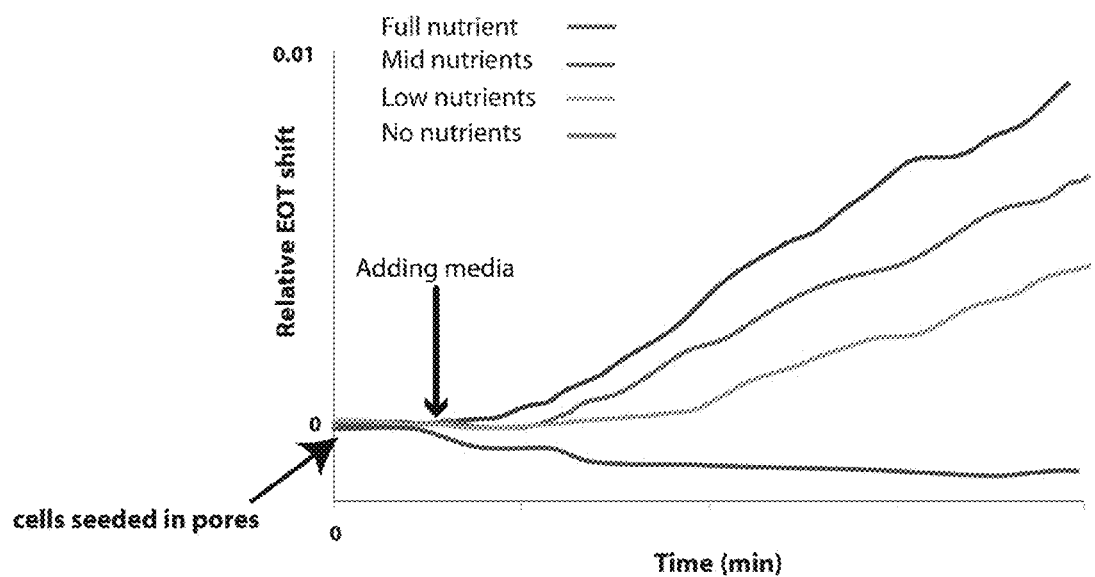

FIG. 9 is a graph showing results of an experiment in which bacterial dependence on nutrients deficiency was monitored. Shown is a relative EOT shift as a function of the time.

Figure 10:
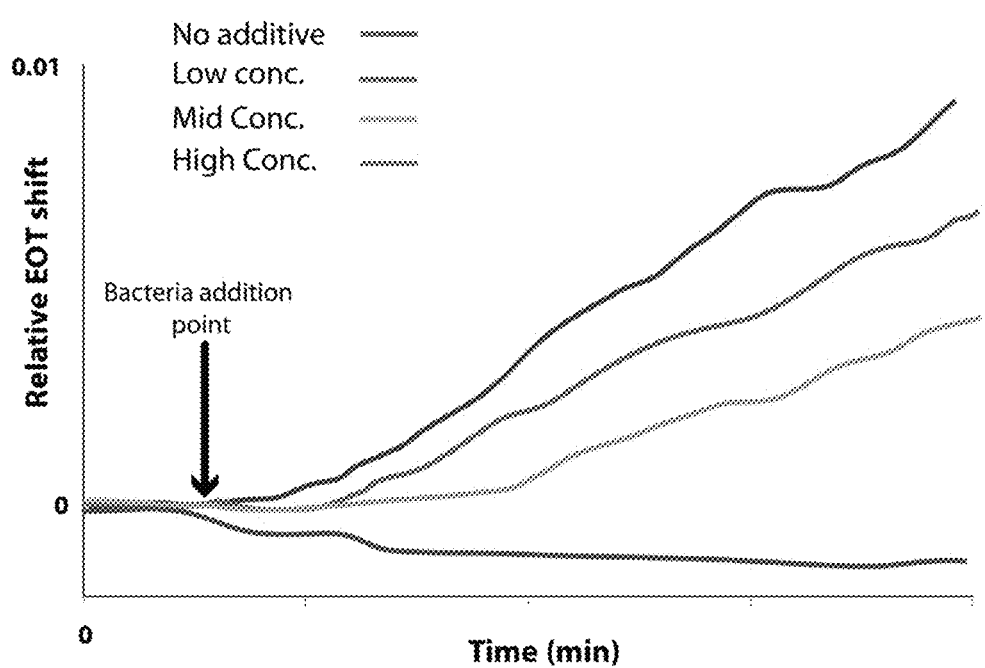

FIG. 10 is a graph showing results of an experiment in which bacterial colonization kinetic in the presence of attachment-preventing drugs was monitored. Shown is a relative EOT shift as a function of the time.

Figure 11:
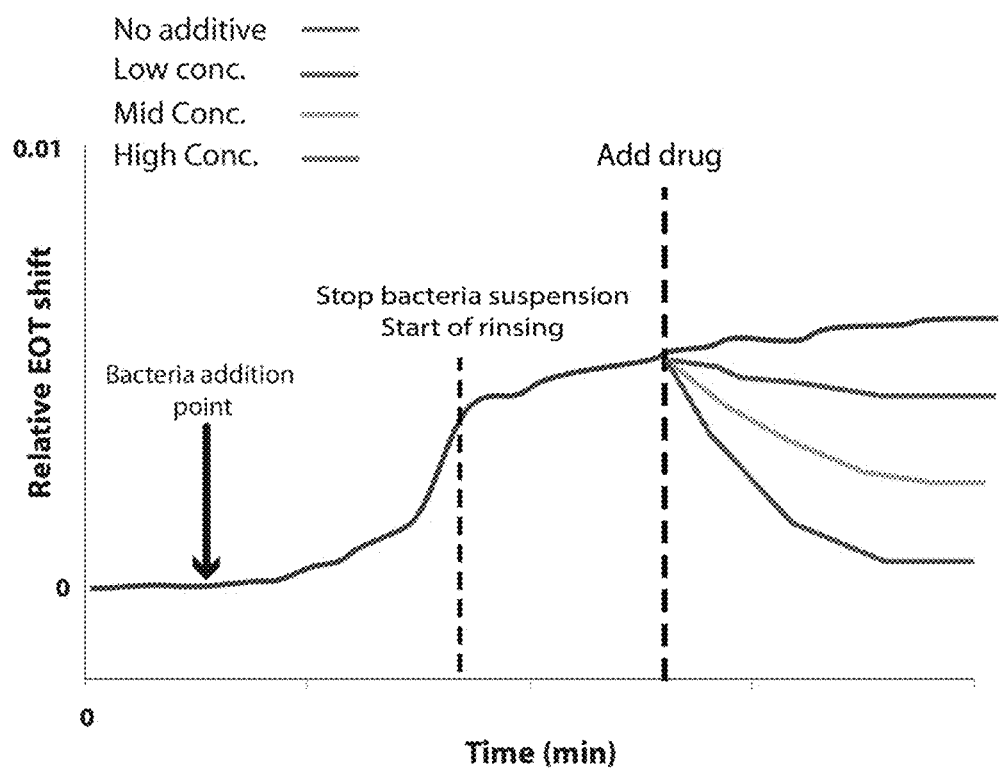

FIG. 11 is a graph showing results of an experiment in which bacterial adherence in the presence of drugs was monitored. Shown is a relative EOT shift as a function of the time.

Figure 12A:
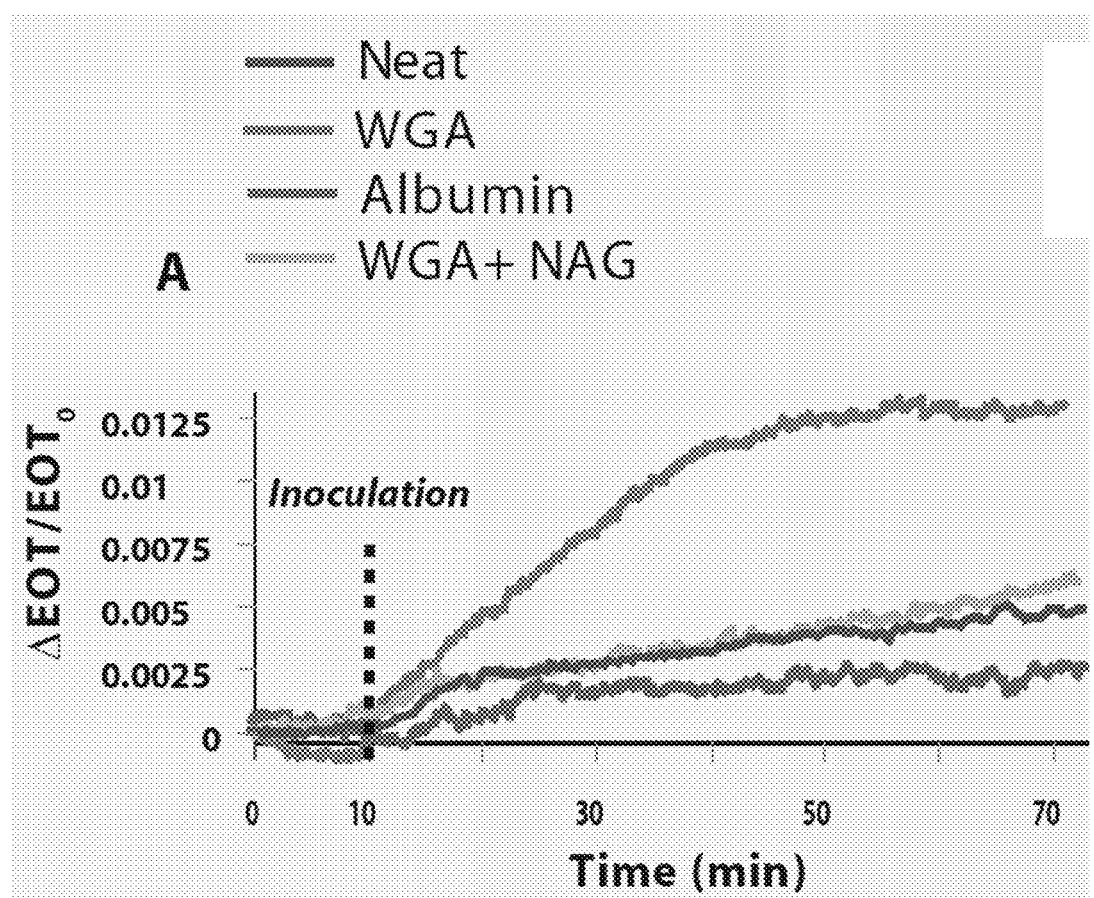
Figure 12B:
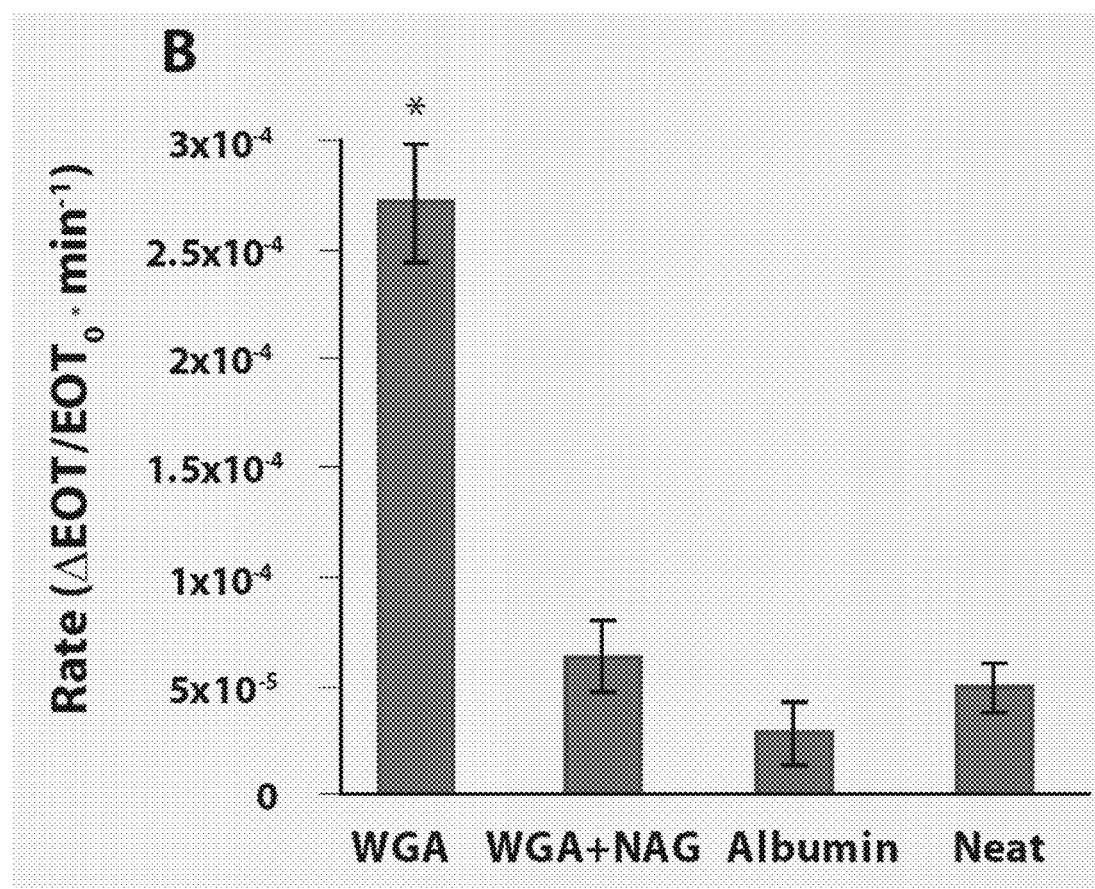

FIGS. 12A and 12B are graph demonstrating that Silicon Photonic Array (SiPA) colonization depends on its surface functionality.

Figure 13A:
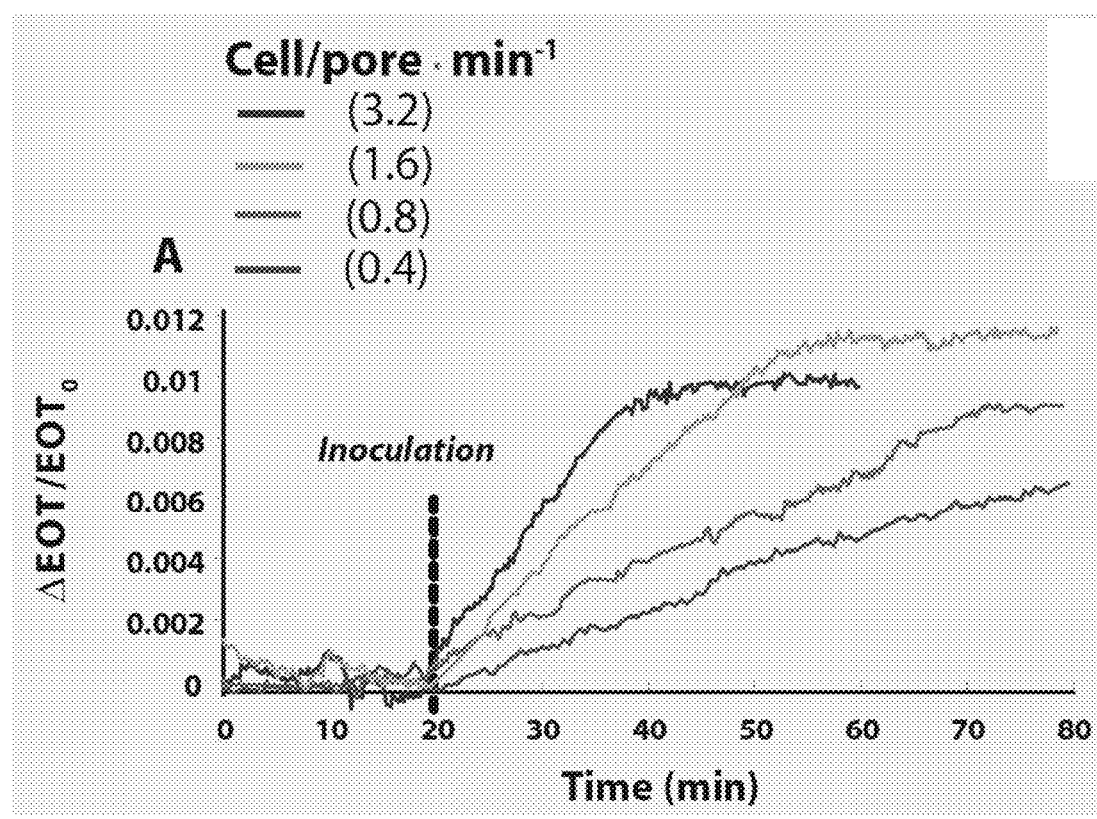
Figure 13B:
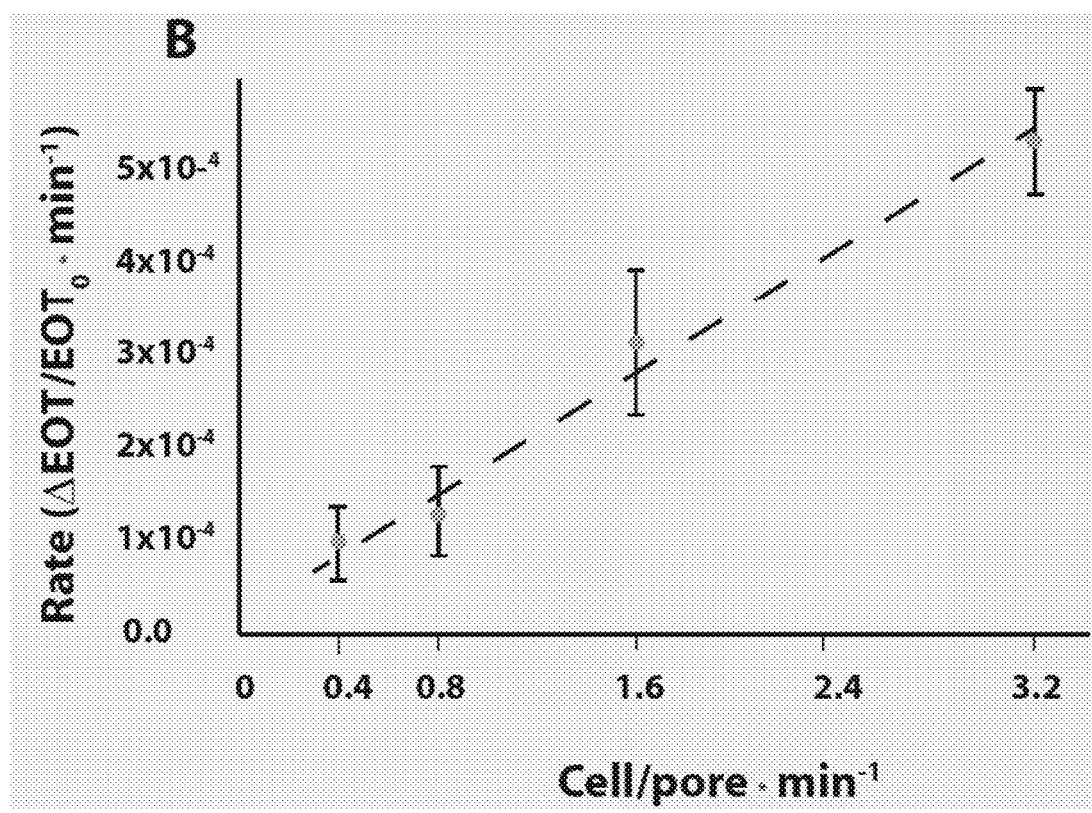

FIGS. 13A and 13B are graphs that demonstrate that SiPA Colonization rate is a function of cell concentration.

Figure 14:
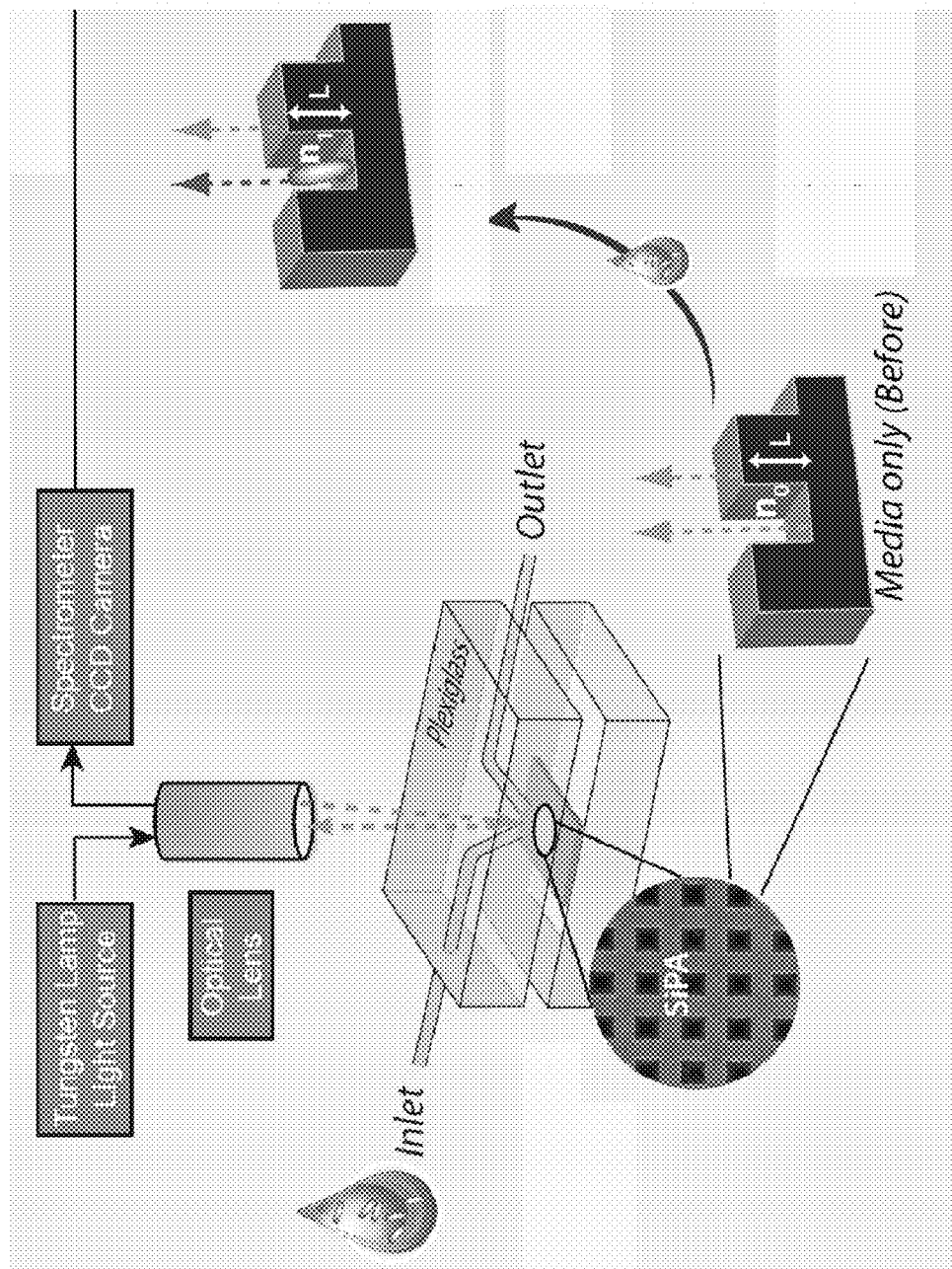

FIG. 14 is a schematic illustration showing experimental and optical principles of a study performed according to some embodiments of the present invention.

Figure 15A:
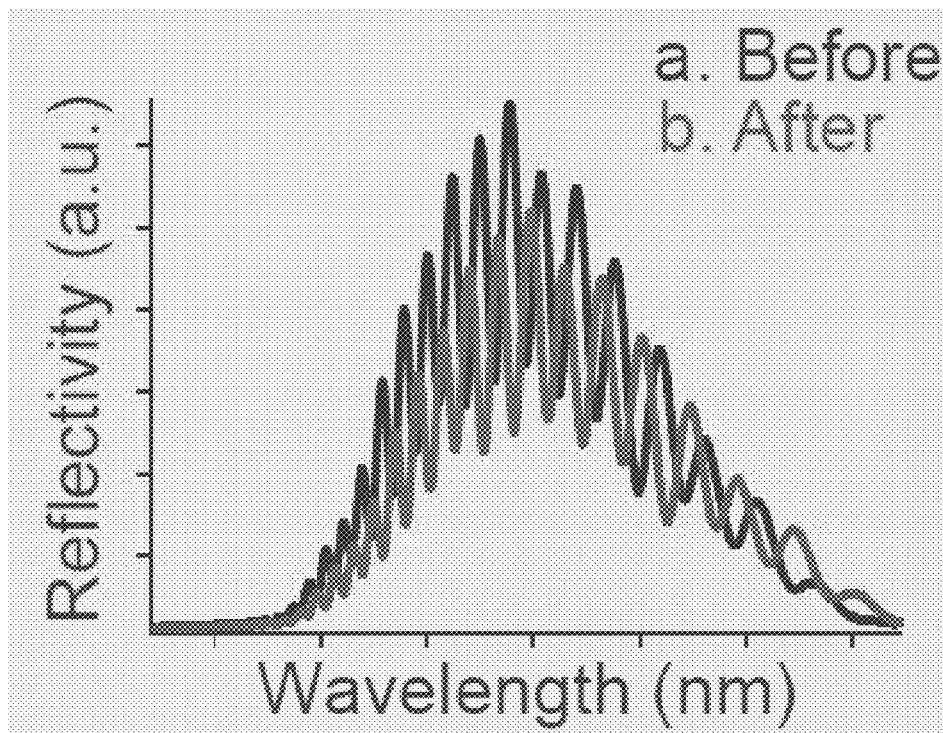

FIG. 15A shows exemplified spectra obtained before and after the introduction of the bacteria into the pores.

Figure 15B:
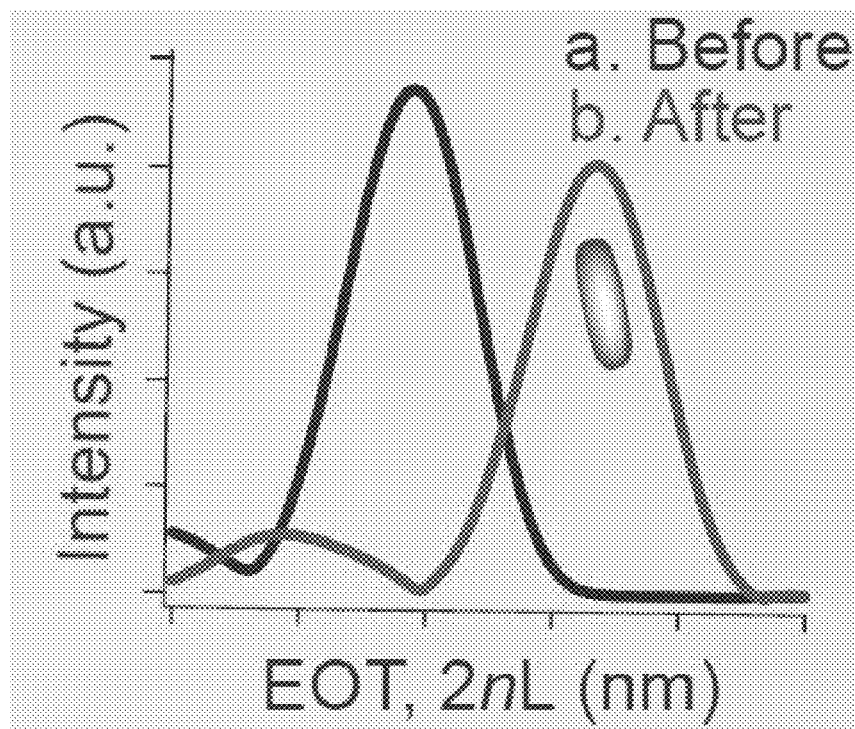

FIG. 15B show FFTs of the exemplified spectra shown in FIG. 15A.

Figure 16A:
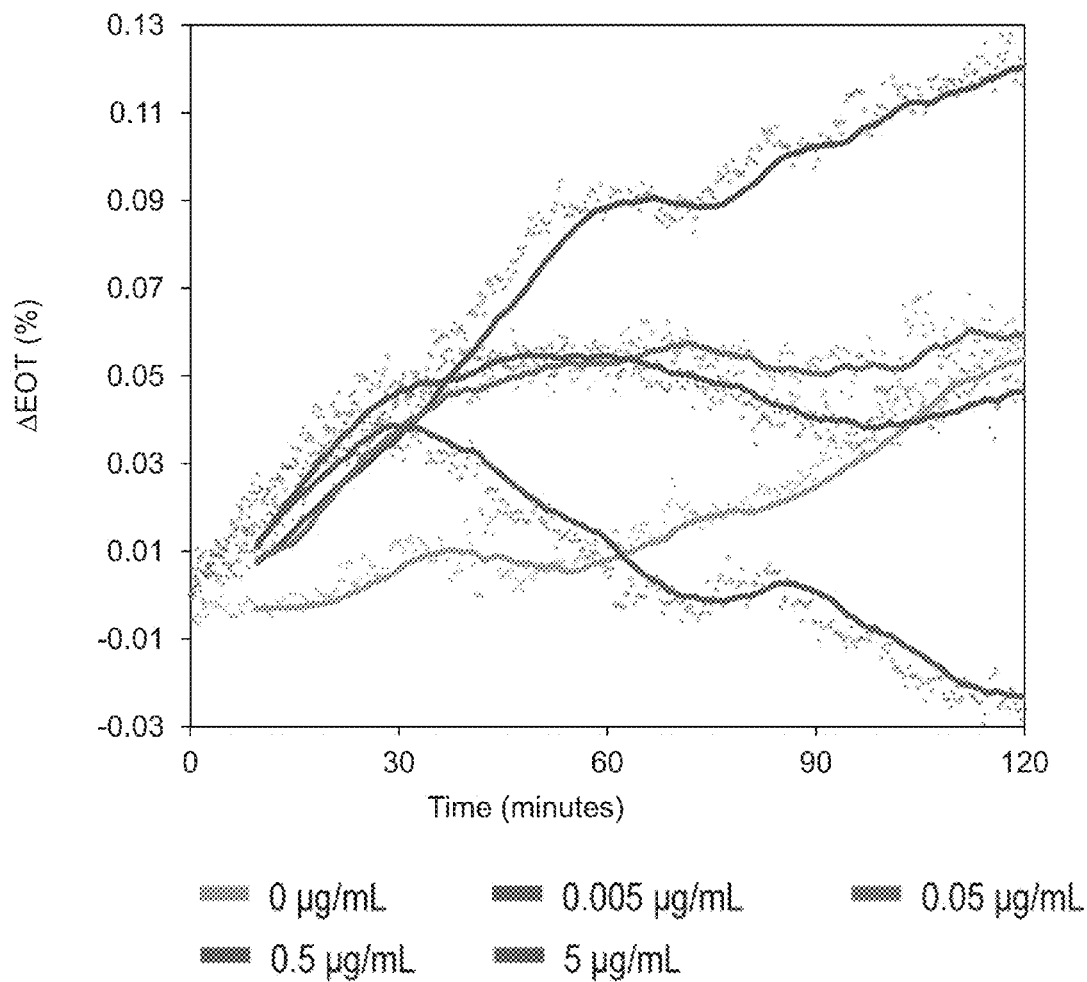
Figure 16B:
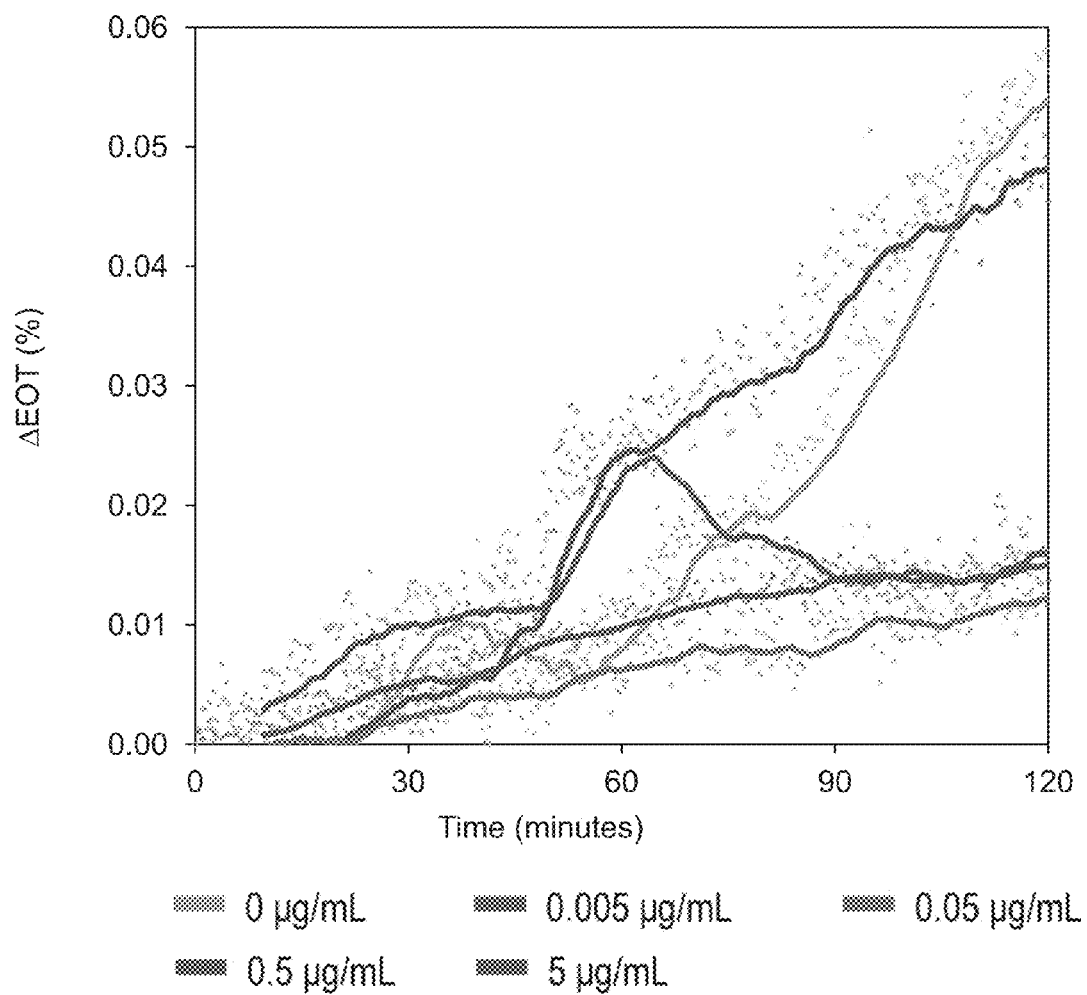
Figure 16C:
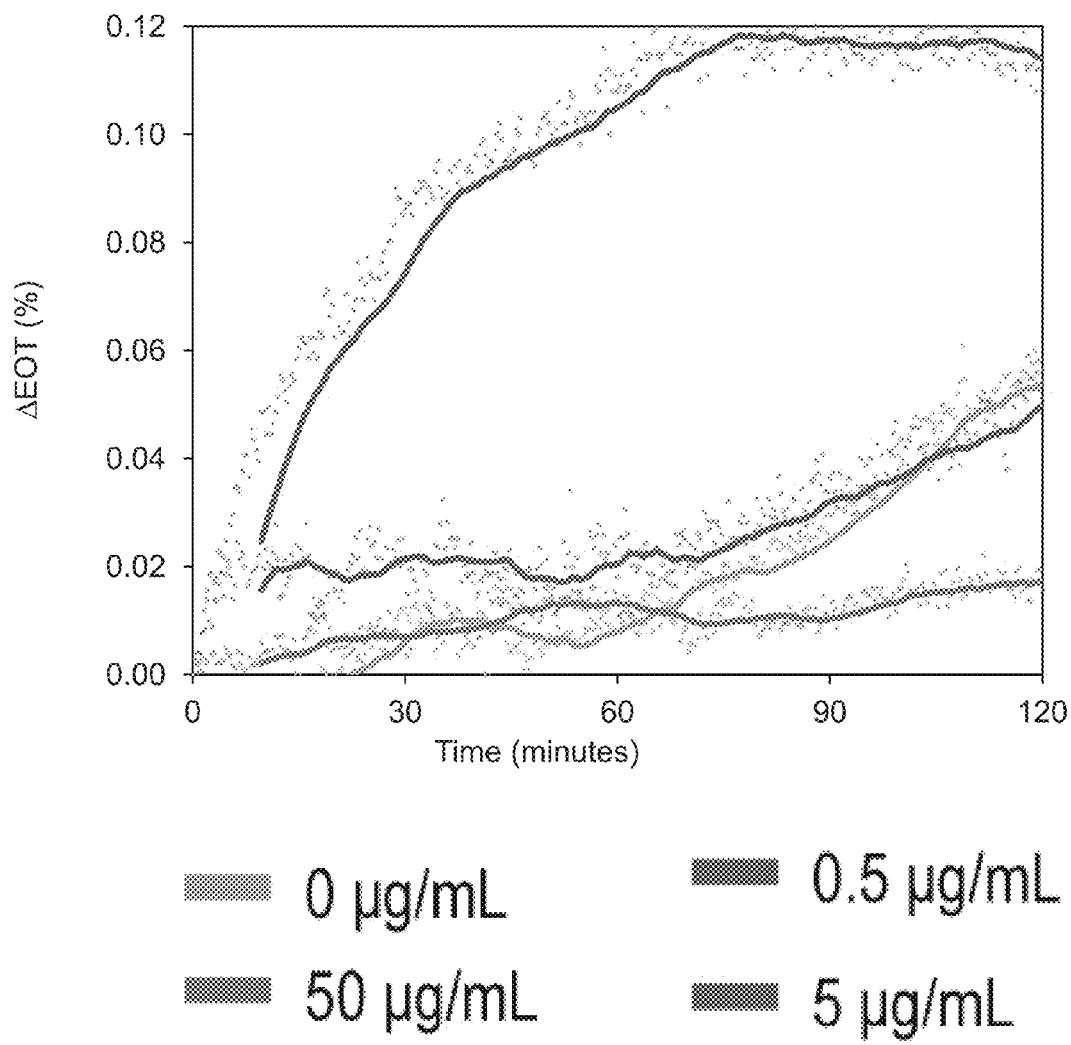

FIGS. 16A-C are graphs showing that the relative changes in effective optical thickness (EOT) directly correspond to growth of bacteria over time. Time 0 represents the point at which the antibiotic was introduced to the bacteria within the photonic microarrays diffraction grating. (a) The MIC of Ceftriaxone Sodium (CRO) was observed to be between 0.005-0.05 µg/mL. (b) The MIC of Ciprofloxacin (CIP) was observed to be between 0.005-0.05 µg/mL. (c) The MIC of Trimethoprim (TMP) was observed to be between 5-50 µg/mL.

Figure 17:
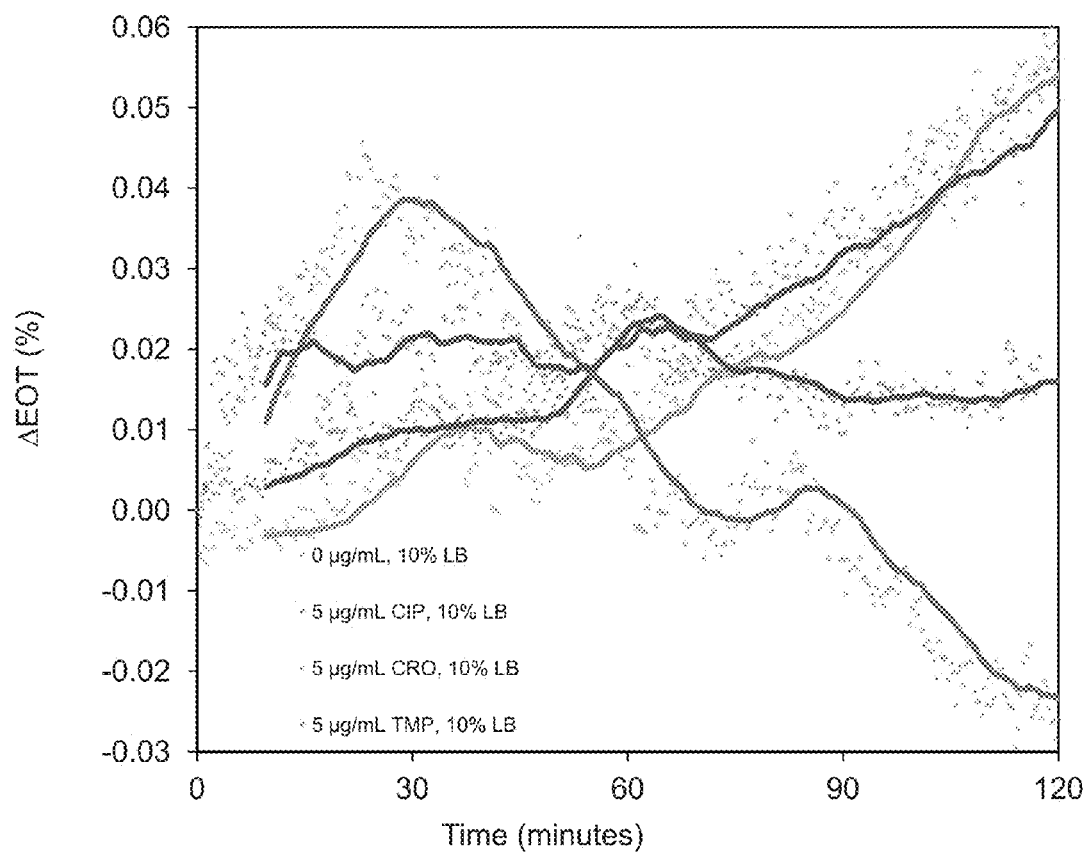

FIG. 17 is a graph showing cross comparison of Ciprofloxacin, Ceftriaxone Sodium, and Trimethoprim at the same concentration. TMP is seen to below the MIC concentration (blue), CIP is bacteriostatic (magenta), and CRO is bactericidal (green) at 5 µg/mL of respective antibiotic.

Figure 18:
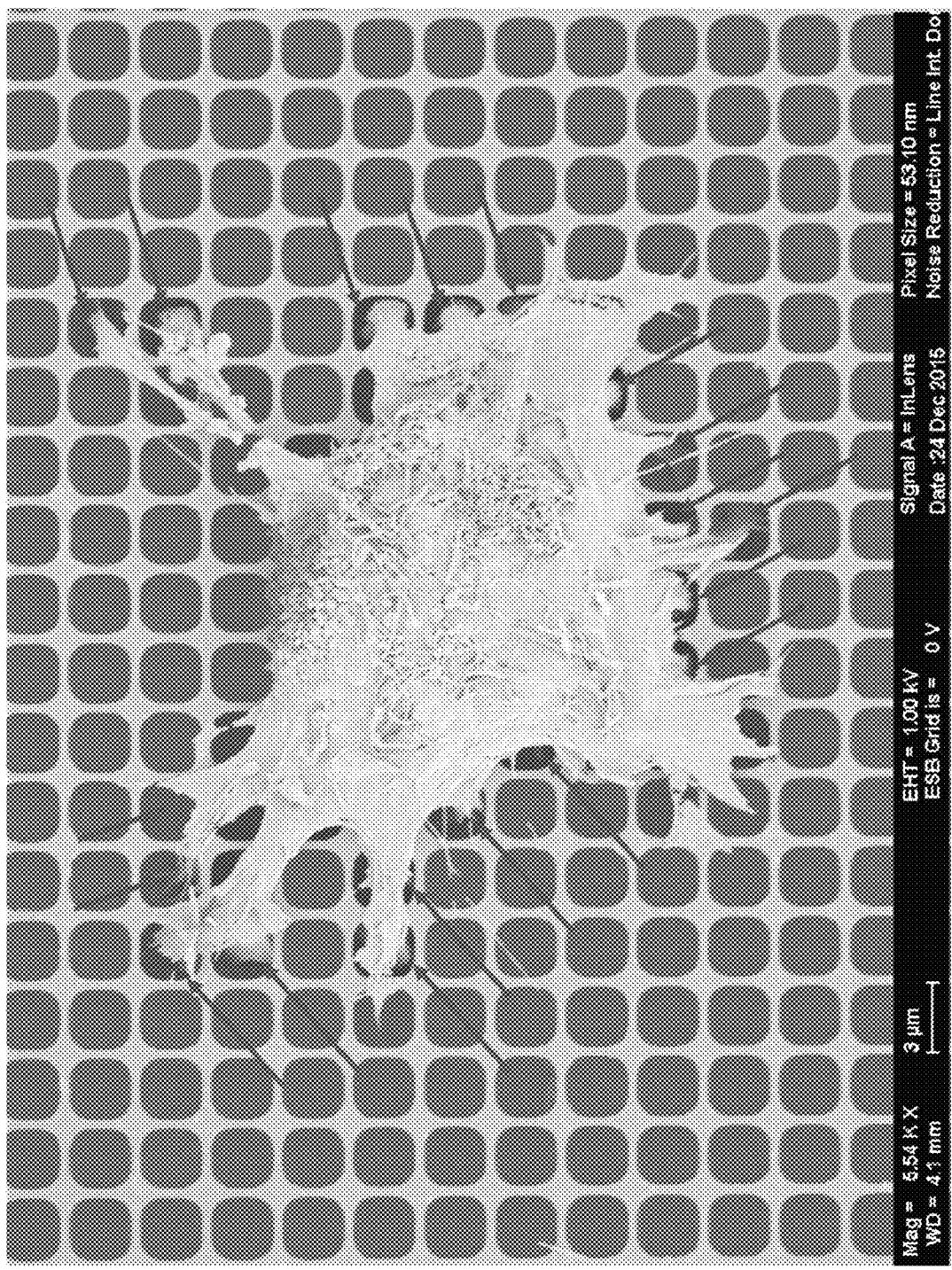

FIG. 18 is an image of a mesenchimal stem cell, grown on photonic microarrays diffraction grating, as imaged by electron microscopy with red arrows pointing at locations where the cell can be seen to penetrate into the compartment.

DESCRIPTION OF SPECIFIC EMBODIMENTS OF THE INVENTION

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

Some embodiments of the invention are described infra and can be used in the implementation of the methods described and claimed herein.

Exemplary methods and systems for the detection and measurement of the concentration of large targets such as micro-organism in the form of cells, bacteria or viruses, or of other large particular biological or other targets are provided.

The methods and systems of the present disclosure are based on the capture of the target elements in pores or micro-compartments, and can be summarized briefly by noting the following characteristics thereof:

(a) Such targets are trapped in pores or micro compartments having sizes selected to accommodate the intended targets, and hence should be at least as large as the targets. In addition, the surface of the micro-compartments or pores can be modified or tailored to enhance the capture and adhesion of the cells to the pores. For example, the surface chemistry of the pores, the roughness of the pore surface and its wettability (either hydrophobic or hydrophilic), can be adjusted for the specific type of target cells and bacteria to be detected.

(b) The order of the pores/compartments is arranged so that light incident thereupon is scattered or reflected, but not randomly, but rather into a set of diffraction orders, such as a diffraction pattern typical of an optical grating. In this case, the zero order of the diffraction pattern as measured by the backscattered light, allows direct sensing of the effective optical thickness (EOT) of the pores/micro compartments. Hence, the zero order of the diffracted light is expected to show an interference pattern that is determined by the EOT of the pores. The depth of the pores can be adjusted to allow sensitive detection of the EOT.

(c) Sensing is achieved by using the changes in the refractive index of the medium in the pores to indicate the presence of target cells within the pores. The medium is usually a liquid or a buffer used to maintain the target cells, and change in the refractive index thereof changes the EOT of the light entering and being reflected from the pores.

(d) One particular method, but not necessarily the only one, to detect the EOT, particularly useful when the EOT is larger than the optical wavelength of the light, EOT>$\lambda$, is by use of Fast Fourier Transform analysis, whereby the spectrum of the reflected light is Fourier transformed to obtain a single intensity peak, whose position characterizes the EOT.

Figure 1A:
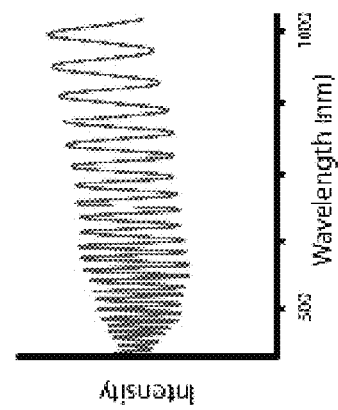
Figure 1B:
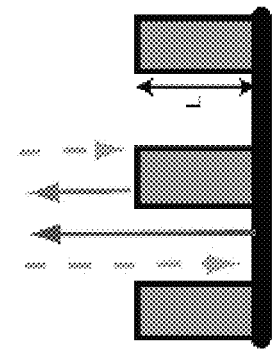
Figure 1C:
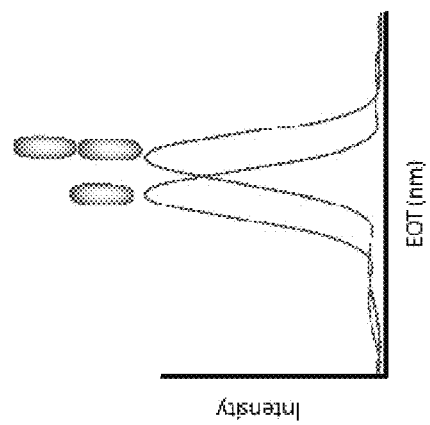
Figure 1D:
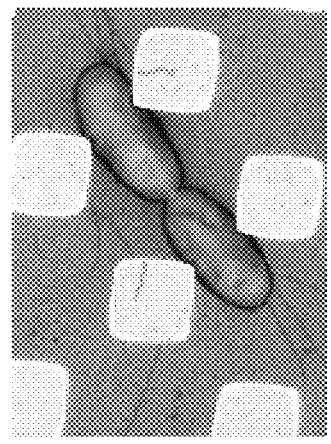
Figure 1E:
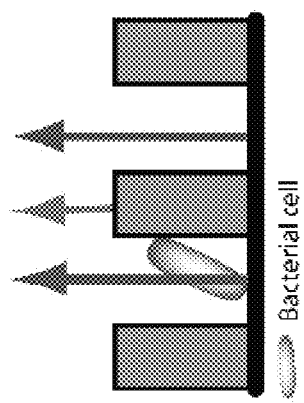
Figure 1F:
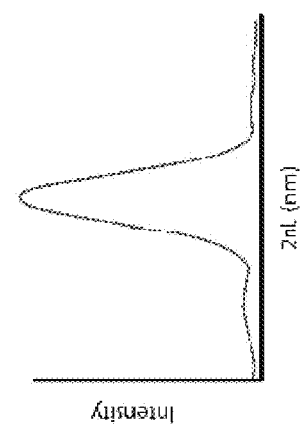

(e) A particularly convenient arrangement for implementing the above described apparatus and methods uses a photonic microarrays diffraction grating, the principle of which is described in FIG. 1A. In some embodiments of the present invention a 2-dimensional periodic Macro-Porous Silicon Array Structure (MPSiAS) is used. A variety of fabrication techniques can be utilized for the fabrication of such a device, such as an electrochemical method or a dry etching method using Reactive-Ion Etching (RIE). It is to be understood, however, that the methods and structures can be implemented by other materials and platforms, such as other semiconductors, organic polymers, gels, glasses and even metallic surfaces.

Consideration is now made of more details of the above described features. Since the size of the targets is equal to or larger than the wavelengths of commonly used light sources (including ultra-violet, visible and near-infrared spectral ranges), conventional PSi substrates with pore sizes large enough to accommodate these targets cannot be used, since, as previously mentioned, the incident optical illumination on a substrate containing a non-ordered assembly of such large pores would result in random scattered light, because of the large size distribution and the random position of the pores. In the apparatus and methods of the present disclosure, a two-dimensional (2D) ordered array of pores or microstructures is used, illuminated in a direction perpendicular to the plane of the pores.

This structure overcomes the problems of optical measurement on pores having sizes larger than the wavelength of the light used for the measurements. Such a structure is effectively a lamellar phase grating, and can be conveniently implemented in the form of a photonic microarrays diffraction grating (e.g., MPSiAS), with pore diameters configured to fit the size of the target. For example, if the typical size of bacterial cells to be captured is in the range of 0.5 to 2$\mu$, the size of the pores or micro-compartments can be fabricated to be in the range of 1 to 10$\mu$, to accommodate those cells. These structures are then used as the optical sensing platform for the detection of the target, such as bacteria cells.

Such periodic structures of PSi photonic crystals, with pore diameters comparable in size to that of bacteria cells may be fabricated by photolithography followed by either electrochemical anodization process (using hydro-fluoric based solution) or by dry etching techniques such as reactive-ion-etching (RIE), to etch the pattern of the pores into standard, commercially available silicon wafers. Both methods are well known in the semiconductor industry and are compatible with standard silicon processing techniques.

The resulting PSi structures act as a lamellar or a phase grating that scatters reflected light into a set of diffraction orders at various angles according to the strict relationship between the periodicity of the grating and the optical wavelength as determined by physical optics. If the reflected light is collected normal to the pores' surface, only the zero-order diffraction is measured. This is usually achieved by using optical lenses having the appropriate f-number and optical fibers for delivering the incident light and collecting the backscattered, zero-order reflected light. In this case, only a phase delay associated with the depth of the pores contributes to the interference pattern created by the backscattered light. This interference pattern is exploited for the measurements of the effective optical thickness (EOT) of the pores.

The presence of target cells within the pores changes the refractive index of the medium in the pores, thus changing the effective optical thickness (EOT) of the pores in the laminar grating. The greater the percentage of macro-pores filled with target cells, the greater the change in the EOT. Thus, measurement of the EOT enables the concentration of target cells in the host solution to be found. Measurement of the EOT of the lamellar grating can be performed in real-time (e.g., within less than an hour or less than a minute or less than a second or less than 100 ms or less than 10 ms or less than 1 ms or less than 100 µs or less than 10 µs or less than 1 µs), by illuminating the photonic microarrays diffraction grating (e.g., MPSiAS) with a polychromatic, preferably broadband, light source. The reflected light spectrum over the wavelength range to be measured is a complex combination of the reflections from the top surface of the photonic microarrays diffraction grating (e.g., MPSiAS) and from the light reflected after passing through the pores and being reflected from their bottom surface. One convenient method by which the reflected spectrum can be measured is by performing Fast Fourier transform (FFT) analysis on this spectrum, by which a single intensity peak is obtained, whose position characterizes the effective EOT of the layer. However, it is to be understood that any other spectral analysis method, or direct optical path difference method may be used. This provides a measurement of the percentage of pores filled by the target cells (sometime called, "the filling factor" of the pores).

Therefore, when the host analyte in the pores are replaced by the target cells to be detected, the EOT changes since the refractive index of the optical media within the wells changes, and hence the position of the output peak of the FFT analysis also changes. The greater the shift in the position of the peak, the higher the concentration of the target cells in the pores. Since the optical measurements can be performed essentially instantaneously, these devices thus provide an effectively real-time measurement of the concentration of target cells in the host solution, the only delay being the time to effectively fill the ordered pore structure with the target cells of the host solution. Furthermore, since the PSi array structure can be readily manufactured by conventional semiconductor technology, the array chip can be provided at low cost for large production runs. Additionally, the optical measurement system is also readily available in the form of a miniature spectrometer, such that the cost of the monitoring system could be substantially less, perhaps by two orders of magnitude, than conventional systems currently used for detecting bio-contamination.

In order to combat the effect of environmental changes, which would result in the shift of the EOT even without any change in the content of the pore structures, a double pore structure can be used, in which the cross sectional dimensions of the inner end of the well, that being the end further from the surface exposed to the host solution, are smaller than the cross sectional dimensions of the outer section of the well. In such a situation, the target cells may be trapped in the outer section, but cannot penetrate the inner narrower section of the wells. However, the host solution does penetrate the inner section and is measured independently of the presence or absence of trapped target cells in the host solution. For such a double well structure, three FFT peaks are detected associated with the effective optical path differences (i) from the surface of the substrate to the bottom of the inner section, (ii) from the surface to the bottom of the outer section, and (iii) between the bottoms of the inner and outer sections. Since the target cell concentration is determined by change in the EOTs (i) and (ii) relative to EOT (iii), while environmental change shifts, to first order, all three of the EOTs equally, the peak associated with the inner section of the wells, EOT (iii) can be used as a base line marker to compensate for environmental change, in particular, change in the ambient temperature. Furthermore, by use of suitable selective coatings, the inner sections can be used to detect secretions from target cells trapped in the outer sections of the wells.

The devices and methods described hereinabove enable the determination of the presence of the target elements trapped in the wells of the photonic microarrays diffraction grating (e.g., MPSiAS), and a quantitative estimate of their comparative level in the host analyte SAME. However, although this may be sufficient information for use in some applications where the target identity is unique, in many applications there could be a number of different target elements, all having similar dimensions, or smaller dimension than the target element, which would enable them to be trapped within the wells, such that the optical analysis performed would not provide information about the specific target identification. Thus, for instance, in a system intended to determine the presence of bacterial pathogens, such as certain strains of *E. coli*, the presence of other bacteria in the analyte, which too could be trapped in the pores of the device, would render the measurement problematic with regard to determining the level of *E. coli*.

Thus, in order to perform such specific assays, it may be advantageous to provide some form of recognition mechanism in order to specifically capture the target micro-organisms which are intended to be detected and measured, thus providing a level of selectivity to the device. Thus, for instance, the surface chemistry of the walls of the wells may be treated to provide a capture probe to trap the micro-organisms which are intended to be measured by the device. They will then remain trapped, while other bacteria and cells will not. The required effect could be obtained by coating with specific antibodies or aptamers or other peptides having a high affinity to the target micro-organism. A bio-mechanism may then be required for ensuring the orientation of the capture probes in the wells such that they trap the incoming bacteria or other cells or organisms. The recognition moiety used will generally be specific for the microorganism to be detected and measured. Therefore, a range of different detection devices can be provided, each being treated with a recognition moiety adapted to the microorganism which it is intended to measure. In principle, the biosensor described in the present disclosure may contain several or even an array of photonic microarrays diffraction gratings (each one could be few μm by few μm, up to few mm by few mm). Each one of these photonic microarrays diffraction gratings can be functionalized for selective detection of a different type of micro-organism, so that a multilevel of bacteria's recognition can be accomplished by this sensor.

The photonic microarrays diffraction grating of the present disclosure can also be used for executing a method of determining the viability of micro-organisms, i.e. in order to differentiate between live and dead cells. Thus, if the device is used for capturing a certain type of bacterial cell, introduction of a growth medium will result in multiplication of the number of live bacteria. This will be reflected in a shift in the EOT signal position, as the effective refractive index of the pores increases.

Although the arrays in this disclosure have been described as being formed in silicon, this being a common and convenient material from which the arrays can be formed, it is to be understand that use of silicon substrates is not intended to limit the invention in any way, and that the invention can be implemented using other materials such as glass, plastic substrates, and fabrication techniques to those described in this disclosure. However, one possible advantage of silicon is the ability to integrate other electronic devices and circuits with the photonic microarrays diffraction grating sensor on the same chip; for example, wireless communication capabilities for remote sensing applications.

Furthermore, although the methods and structures of this disclosure are generally described as applied to the detection of biological targets having dimensions of the same order as or somewhat larger than the wavelength of the light used for the detection, it is to be understood that these methods and structures are not intended to be limited to such biological targets, but are understood to be applicable to the detection of targets of suitable size of any type, whether biological or not. Such other applications could be found in the fields of water technologies, environmental pollution measurement, chemical industries, and others.

Furthermore, since white light or polychromatic, preferably broadband, sources having a range of wavelengths should be used in the apparatus described in the present disclosure, and for performing the methods of the present application, and such sources may have wavelengths which stretch out well beyond the region in which the spectral detection is performed, it is to be understood that reference, both in the disclosure and as claimed, to the wavelength of light or illumination being used to perform the detection is understood to refer to wavelengths where the majority of the energy of the source is concentrated, such as the wavelength at the point of peak intensity, or the mean wavelength of the spectral region containing the majority of the optical intensity, or the wavelength of maximum sensitivity of the detector, or similar definitions. In any event, the term wavelength of the incident illumination and expressions having similar meaning is not intended to include limitations based on wavelengths at extreme ends of the source's emitted spectrum, where the detection efficiency or the illumination level is impractically low.

Additionally, the traps into which the target elements enter and are captured, and whose effective optical depths are measured, have been variously described in this disclosure as pores, micro-compartments and wells, all of which are understood to relate to the same feature. The term well is used in the claims as a simple generic term to represent any of these features.

There is thus provided in accordance with an exemplary implementation of the devices described in this disclosure, a system for detecting target elements in a host analyte, the system comprising:

(i) a substrate containing an ordered array of wells formed in its surface, at least some of the wells having lateral dimensions such that the target elements can fit therein, (ii) a polychromatic, preferably broadband, illumination source emitting a range of wavelengths, disposed so as to illuminate the surface of the substrate, (iii) an optical detector disposed such that it collects light diffracted from the substrate, and outputs a reflected spectrum signal, and (iv) a signal processing unit, adapted to analyze the reflected spectrum signal to provide a measure of the effective optical depth of the wells, wherein at least some of the wells have a lateral dimension at least as large as the wavelengths of the illumination source detected by the optical detector.

In such a system, the signal processing unit may analyze the reflected spectrum signal using the Fast Fourier Transform. In such a case, the effective optical depth is determined from the position of a peak obtained from the results of that Fast Fourier transform analysis on the reflected spectrum. Furthermore, the optical detector may be disposed normal to the substrate, such that it collects diffracted light of zero order from the substrate.

Additionally, in alternative implementations of the above-described systems, the effective optical depth of the wells may provide an indication of the concentration of the target elements captured within the array of wells, and hence also an indication of the concentration of the target elements in the analyte.

In any of the above described systems, the ordered array of wells may comprise a lamellar photonic crystal grating. Additionally, the substrate may a silicon chip, and the ordered array of wells may be constructed by microelectronic fabrication processes.

Additional implementations may involve a system such as those previously described, in which the target elements are bacterial cells having dimensions larger than the wavelengths of the illumination source detected by the optical detector element. The wells may comprise capture probes having a high affinity to the target cells intended to be measured by the system. Such capture probes may be coated on the walls of the wells. As specific examples, the target elements may be micro-organisms, and the capture probes may then be any one of antibodies, aptamers or other peptides. These microorganisms may be bacterial cells, and the capture probes specific antibodies. Furthermore, the wells may incorporate a cell nutrient supply, such that the growth of the microorganisms can be observed after application of the nutrient supply. Lack of growth of the microorganism after application of the nutrient supply can then be used as an indication that the microorganism is generally dead. Furthermore, in any of these systems, at least some of the wells may include a recognition moiety adapted to the target elements to be detected. If so, then the substrate may comprise at least two different regions, the wells in each of the regions including a different recognition moiety, such that each of the different regions can detect different target elements concurrently.

In general, any of the above described systems may be adapted to provide real time detection of microorganisms (e.g., detection of microorganisms in less than an hour or less than a minute or less than a second or less than 100 ms or less than 10 ms or less than 1 ms or less than 100 μs or less than 10 μs or less than 1 μs).

Another example implementation can involve a system such as any of those previously described, in which at least some of the wells have at least two sequential sections having different lateral dimensions, and wherein a second section, further from the surface than a first section, has a lateral dimension less than that of the first section. In such a configuration, the dimensions of the second section may be such that the target elements cannot penetrate the second section, while the host analyte can. In this case, change of the measured effective optical depth of the second section of at least some wells may be utilized as a marker to compensate for changes in environmental conditions that cause the effective optical depth of both of the first and second sections to change. The second section may be provided with sensitivity to a material which targets trapped in the first section may secrete. In this case, the sensitivity may be utilized to provide further information regarding the level of targets trapped in the first sections of the wells.

Yet other implementations perform a method for detecting target elements in a host analyte, the method comprising:

(i) providing a substrate containing an ordered array of wells formed in its surface, (ii) illuminating the surface of the substrate with polychromatic, preferably broadband, illumination, (iii) detecting light diffracted from the substrate and generating therefrom a reflected spectrum signal, and (iv) determining from the reflected spectrum signal a measure of the effective optical depth of the wells, wherein at least some of the wells have a lateral dimension larger than the wavelength of the detected polychromatic, preferably broadband, illumination.

In such a method, the step of determining from the reflected spectrum signal a measure of the effective optical depth of the wells, may be performed by Fast Fourier Transformation analysis. In any case, the detecting may be performed normal to the substrate, such that light of zero order diffracted from the substrate is detected. The target elements may be bacteria, and the host analyte may be any one of water, a buffer solution, blood, urine or a solution derived during a food process.

In some implementations of this method, at least some of the wells may have at least two sequential sections having different lateral dimensions, and a second section, further from the surface than a first section, should have a lateral dimension less than that of the first section. In such a method, the dimensions of the second section may be such that the target elements cannot penetrate the second section, while the host analyte can. Any such method may further comprise the step of detecting change in the effective optical depth of the second section of at least some of the wells, such that compensation can be made for changes in environmental conditions that cause the effective optical depth of both of the first and second sections to change.

Preferred embodiments of the present invention provide a method suitable for determining a phenotype of cells. In these embodiments the cells are placed in a plurality of compartments forming a periodic array (e.g., diffraction grating) on a substrate. A polychromatic light beam is preferably diffracted off the periodic array. The diffraction can be reflective or transmissive as desired. Based on a diffraction pattern received from the periodic array, a parameter indicative of the refractive index of the cells is preferably calculated.

For example, the parameter can be the EOT or a proxy thereof, and the change of the parameter can be the change in the value of the EOT relative to its value in the absence of the cells. The change in the value of the EOT relative to its value in the absence of the cells is optionally and preferably expressed as $\Delta EOT/EOT_0 = 2(\Delta n/n_0)L$, where $n_0$ is the refractive index of the compartments before the introduction of the cells into the components, $\Delta n$ is the change in the refractive index as a result of the introduction of the cells into the compartments, and $EOT_0$ is the EOT before introducing the cells into the compartments.

The time-dependence of a change of the parameter is then determined, and the phenotype of the cells in the biological sample is determined based on the time-dependence.

Ideally, the obtained pattern and calculated parameter is continuous resulting in a continuous set of values of the parameter over a continuous time interval. However, such continuous set of values is rarely attainable, and in practice a plurality of values of the parameter is obtained at a plurality of discrete time instances. The number of values is nevertheless sufficient for obtaining (e.g., by interpolation) the time-dependence of the parameter over a predetermined time period (e.g., from several minutes to several hours). Thus, a sequence of samples of the parameter is generated at various time-instances separated from each other by sufficiently short time-intervals. The obtained time-dependence is a mathematical function which expresses the value of the parameter as a function of time t, for at least a few instances within the predetermined time period $[t_1, t_2]$. The mathematical function may also be a continuous function expressing the value of the parameter as a function of time, for any time $t \in [t1, t2]$.

In various exemplary embodiments of the invention the obtained sequence of the parameter's values is subjected to an initial signal processing, such as, but not limited to, Fourier transform, fast Fourier transform, autocorrelation processing, wavelet transform and the like. The purpose of the initial processing is to delineate the components of the mathematical function at a particular domain and to allow removing the undesired components from further processing. For example, a Fourier, fast Fourier or wavelet transform can be used to delineate the various frequency components of the time-dependence, and to remove those frequency components identified as noise.

The determination of the phenotype can be done by means of a database of reference time-dependences. The database can be stored on a non-transitory computer readable medium. Such a database can include one or more entries, each entry can include a database phonotype and a database time-dependence associated with this phonotype. The database time-dependence can be in the form of a graph, or in the form of a set of characterizing parameters that characterize the time-dependence as further detailed hereinbelow. In embodiments in which an initial signal processing is employed, the database time-dependences preferably correspond to this initial signal processing. Several exemplified database entries are shown in the plots of FIGS. 4, 5A, 5B, 6A, 7-11, 12A and 13A, where each plot line can be a database time-dependence, and the associated legend can represent a phenotype.

The method can access the computer readable medium storing the database and search the database for a database time-dependence that best matches the obtained time-dependence. The matching can be by graph comparison techniques (e.g., by calculating sum of squares of distances between points over the time-dependences). When the database time-dependence is in the form of a set of characterizing parameters, the characterizing parameters of the database time-dependence can be compared, optionally and preferably one-by-one, to the characterizing parameters of the obtained time-dependence.

In some embodiments of the present invention the time-dependence of the calculated parameter (e.g., the EOT, or the change of EOT with respect to its value in the absence of the cells) is characterized by the method using one or more characterizing parameters that are extracted from the obtained time-dependence. The characterizing parameters may comprise, for example, values of the calculated parameter at transition points on the time-dependence. Generally, a transition point is identified on the time-dependence of the calculated parameter as points in which a functional transition occurs.

As used herein "functional transition" refers to any detectable mathematical transition of a function, including without limitation, a transition of a given function (e.g., a change of a slope, a transition from increment to decrement or vice versa) and a transition from one characteristic functional behavior to another (e.g., a transition from a linear to a nonlinear behavior or a transition from a first nonlinear behavior to a second, different, nonlinear behavior).

The functional transitions can be identified, for example, by calculating a derivative of the time-dependence and finding zeros thereof. As will be appreciated by one of ordinary skill in the art, a transition of a function can be characterized by a zero of one of its derivatives. For example, a transition from increment to decrement or vice versa is characterized by a zero of a first derivative, a transition from a concave region to a convex region or vice versa (points of inflection) is characterized by a zero of a second derivative, etc. Any derivative of the time-dependence can be used. Generally, the functional transitions can be characterized by a sign inversion of an nth derivative of the time-dependence, where n is a positive integer.

Additionally or alternatively, the functional transitions can be identified by observing deviations of the time-dependence from smoothness. In this embodiment, the functional transitions can be identified either with or without calculating the derivatives of the time-dependence. For example, deviations from smoothness can be identified by comparing the time-dependence to a known smooth function.

As used herein the phrase "biological sample" refers to any sample which comprises viable cells. In some instances the term analyte is interchangeably used with biological sample.

According to a specific embodiment, the biological sample may be a clinical sample. The biological samples may be used directly or may be used in diluted forms.

The biological sample may be a clinical sample, a laboratory sample or an environmental sample, According to a specific embodiment, the biological sample is a sample obtained from body fluid, like sputum, saliva, blood, or a tissue derived biological sample obtained by extraction, isolation or purification from a tissue or body fluid source.

According to a specific embodiment, the biological sample is feces, urine, blood, sputum or saliva. For example, the sample obtained from an individual may be used in diluted or undiluted form. Dilution (of any biological sample) may be effected with physiological acceptable liquids like saline or suitable culture medium, e.g. a rich culture medium. Optionally, cells analyzed according to the present teachings may be isolated in advance according to generally known methods.

Alternatively, or additionally the biological sample may be a laboratory inoculums or specimen or a laboratory preparation such as a bacterial or eukaryotic cell culture.

Alternatively or additionally, the biological sample is from an industrial source.

For example, the biological sample may be from the food industry e.g., dairy, meat and the like.

Alternatively or additionally, the biological sample (an environmental sample) comprises waste water, fresh water, brine, salt water. A sample collected from surfaces (e.g., filters, animal houses, hospital equipment etc.).

As used herein "cells" refers to a eukaryotic cell or a prokaryotic cell or parts thereof as exemplified below.

According to a specific embodiment, the cell is of a microorganism e.g., bacteria, fungi, yeast.

The prokaryotic cell may be a bacterial cell or a blue-green algal cell.

According to a specific embodiment, the bacterial cell may be a Gram positive cell or a Gram negative cell. According to a specific embodiment, the bacterial cell is of a pathogenic bacteria.

According to a specific embodiment, the bacteria belong to a species selected from the group consisting of (but not limited to) *Staphylococcus aureus, Streptococcus pyogenes* (group A), *Streptococcus* sp. (*viridans* group), *Streptococcus agalactiae* (group B), *S. bovis, Streptococcus* (anaerobic species), *Streptococcus pneumoniae*, and *Enterococcus* sp.; Gram-negative cocci such as, for example (but not limited to), *Neisseria gonorrhoeae, Neisseria meningitidis*, and *Branhamella catarrhalis*; Gram-positive bacilli such as *Bacillus anthracis, Bacillus subtilis*, P. acne *Corynebacterium diphtheriae* and *Corynebacterium* species which are diptheroids (aerobic and anaerobic), *Listeria monocytogenes, Clostridium tetani, Clostridium difficile, Escherichia coli, Enterobacter species, Proteus mirablis* and other sp., *Pseudomonas aeruginosa, Klebsiella pneumoniae, Salmonella, Shigella, Serratia, Rathybacter, Leifsonia, Clavibacter* and *Campylobacter jejuni*.

According to a specific embodiment, the pathogenic bacteria are selected (but not limited to) from vancomycin-resistant *enterococcus* (VRE), pneumococcal species, methicillin-resistant *Staphylococcus aureus*, multi-drug resistant *Staphylococcus aureus* (MDRSA), multi-drug resistant *Pseudomonas* species, *Nesseria* sp., *Hemophilus* sp., *Proteus* sp., *Klebsiella* sp. and *Esherichia coli*. Preferably, the pathogenic bacteria are selected from VRE, MDSA, and multi-drug resistant *Pseudomonas*.

According to a specific embodiment, the bacterial cell is of a non-pathogenic bacteria.

According to a specific embodiment the bacteria is a non-pathogenic mutual, commensual, probiotic strain of bacteria or a microbiome strain.

The euykaryotic cell may be a cell line or a primary cell of a unicellular or a multicellular organism. According to a specific embodiment, the cell is a non-pathogenic cell (e.g., cancer cell, immune cell). The eukaryotic cell may be a differentiated cell or a non-differentiated stem cell (e.g., pluripotent stem cell, hematopoietic cell, mesenchymal stem cell) or a progenitor cell. According to a specific embodiment, the cell is a pathogenic cell. Examples of eukaryotic cells that can be used according to the present teachings include, but are not limited to protozoan, yeast cells, plant cells, fungal cells, animal cells e.g., mammalian cells (e.g., primate cells or human cells) or insect cells and the like.

According to a specific embodiment, the cell is isolated from a subject in need thereof, e.g., for personalized therapy.

The cell may be a naturally occurring cell or genetically modified (e.g., infected, transfected or transformed to express a heterologous genetic element) or otherwise modified (e.g., chemically or physically).

According to a specific embodiment, the cell is in suspension.

According to another embodiment, the cell forms a part of a tissue fragment or a cell aggregate. It will be appreciated that there is no need for the cells to enter the microarrays one at the time or in whole. For mammalian cells it is sufficient that just part of the cells would enter, e.g. cytoplasmic extension, cilia, villi, dendrite and the like. For clarity, FIG. 18 shows a mesenchymal stem cell laying above the gratings with extensions entering the compartments.

The number of cells or cell fractions in each compartment is determined according to the compartment size.

According to a specific embodiment, the cell is genetically modified with a genetic element e.g., for upregulation (over-expression) or down-regulation (silencing) of a gene of interest. According to a specific embodiment such a modification imparts the cell with a growth advantage such as tolerance to stress, oncogenic transformation and the like. Alternatively, such a modification imparts the cell with a growth disadvantage.

As used herein the term "phenotype" refers to any characteristic or trait of the cell which can be observed according to the present teachings.

According to a specific embodiment, the phenotype is selected from the group consisting of viability, motility, biofilm production, colonization, protein production and lipid production.

As used herein "viability" refers to the determination if the cell is alive or dead. According to the present teachings viability is determined in a time dependent manner, in such instances viability is also referred to as replication rate or growth rate. In other instances it is referred to as apoptosis rate or necrosis rate.

According to a specific embodiment, the phenotype is not viability.

According to a specific embodiment, the phenotype is viability in the presence of a test agent, e.g., drug, e.g., antibiotic to determine antibiotic resistance e.g., of bacterial, fungal, cancer cells.

As used herein "motility" refers to the ability of a cell to migrate. Motility refers to a spontaneous or an active movement (e.g., towards a chemokine) that typically, consumes energy in the process.

As used herein the term "biofilm formation" refers to the adherence of microorganisms to each other and often to a surface. These adherent cells are frequently embedded within a self-produced matrix of extracellular polymeric substance (EPS). According to the present teachings biofilm formation affects the refraction index and therefor the EOT.

Many different bacteria form biofilms. Examples include, but are not limited to gram-positive (e.g. *Bacillus* spp, *Listeria monocytogenes, Staphylococcus* spp, and lactic acid bacteria, including *Lactobacillus plantarum* and *Lactococcus lactis*) and gram-negative species (e.g. *Escherichia coli*, or *Pseudomonas aeruginosa*). Biofilms are formed by bacteria that colonize plants, e.g. *Pseudomonas putida, Pseudomonas fluorescens*, and related pseudomonads which are common plant-associated bacteria found on leaves, roots, and in the soil, and the majority of their natural isolates form biofilms. Several nitrogen-fixing symbionts of legumes such as *Rhizobium leguminosarum* and *Sinorhizobium meliloti* form biofilms on legume roots and other inert surfaces.

As used herein "colonization" refers to the establishment or settlement of a colony of micro-organisms at a particular site. If circumstances are favorable to the microorganism, numbers may increase rapidly.

According to the present teachings colonization is determined by the establishment of a single or colony of micro-organisms at any site within the microarray, e.g. SiPA.

As used herein "protein production" refers to intracellular protein accumulation such as in bacterial inclusion bodies.

As used herein "lipid production" refers to intracellular lipid accumulation such as in storage disorders.

As used herein "RNA production" refers to intracellular RNA (e.g., mRNA) accumulation.

Each or protein accumulation, RNA production and lipid accumulation affects the EOT.

Other phenotypes that can be monitored are shrinkage, lysis, cell wall integrity and the like.

Distinguishing between the different phenotypes can be done using various assay conditions, such as in the presence migration inhibitors, protein synthesis inhibitors and the like to distinguish between the phenotypes.

In order to determine a phenotype, the cells are placed on the diffraction gating in a growth medium, which composition is determined based on the analyzed phenotype. Control medium typically includes the cells growth medium, from which a calibration curve can be obtained according to the present teachings.

According to a specific embodiment, the present teachings are directed at determining the effect of a test agent on the cells (i.e., on the phenotype of the cells).

As used herein, a test agent refers to a chemical or biological agent or alternatively a physical condition.

The chemical agent may be a synthetic or naturally occurring molecule e.g., small molecule, The biological agent, may be a synthetic or naturally occurring nucleic acid (e.g., polynucleotide, oligonucleotide, DNA editing agents, RNA silencing agents e.g., ddsRNA, miRNA, siRNA, aptamers) or proteinaceous agent (e.g., antibodies, peptides).

The physical condition may refer to any physical treatment including, but not limited to pressure, temperature shift, radiation and the like.

According to a specific embodiment, the test agent is selected from the group consisting of an antibiotic, a chemotherapy, a radioisotope, a herbicide and a fungicide.

According to a specific embodiment, the agent may penetrate into the cell or modified to penetrate the cell.

According to a specific embodiment, the agent does not penetrate into the cell.

According to a specific embodiment, the test agent is a cytostatic agent.

Such agents cause the inhibition of cell growth and multiplication.

Chemotherapy of cancer, treatment of skin diseases and treatment of infections are common use cases of cytostatic drugs. Active hygienic products generally contain cytostatic substances.

A variety of cytostatic antibiotics are used in the treatment of hyperproliferative diseases such as cancer. Examples include, but are not limited to doxorubicin (Caelyx), daunorubicin (Cerubidin), dactinomycin (Cosmegen Lyovax), epirubicin (Pharmorubicin) and idarubicin (Zavedos).

According to a specific embodiment, the agent is a cytocidal agent that causes cell death. Examples of cytocidal agents include, but are not limited to, CY, DDP, VCR, Ara-C, which are often used for cancer treatment.

The test agent may be added to the compartments such that it is immobilized thereto, i.e., the diffraction gating comprises the test agent adhered to the compartments.

Alternatively or additionally, the test agent is in the biological sample (i.e., not immobilized to the compartments).

As mentioned, evaluating the phenotype also in the absence of the test agent is typically preferred. Such an evaluation is typically used as control.

According to some embodiments of the present invention an induced change in the time-dependence in the presence of the test agent relative to the absence of the test agent is indicative of an effect of the test agent on the phenotype of the cells in the biological sample.

The test agent may be added to the diffraction grating prior to the addition of the cells.

Alternatively, the cells are incubated with the diffraction grating so as to fill the compartments prior to adding the test agent.

According to a specific embodiment, when the time-dependence is indicative of a decrease in the change in EOT relative to its value in the absence of the cells, said test agent is a cytocidal agent.

According to a specific embodiment, when the time-dependence is substantially flat the test agent is a cytostatic agent.

As used herein, "flat time-dependence" means that the maximal variation of the respective quantity (parameter, change of parameter) over a time-period of X minutes is less than Y % of the maximal value of the respective quantity over this time-period, where X is at least 1 or at least 10 or at least 20 or at least 40 or at least 60, and Y is about 20 or about 15 or about 10 or about 5 or less.

Based on the present teachings, the present inventors were able to determine the effect of selected agents on cell phenotype. The present systems are sensitive enough to determine the effective amount to achieve the phenotype as shown in FIGS. 16A-C and 17.

Thus, the present teachings allows monitoring a cellular phenotype as a function of time and not as a single incident (even though in real time), rather as continuous change in their phenotype optionally in response to a test agent.

This is done by monitoring the rate of relative change in the physical properties of the cells e.g., cell volume and composition.

The rate by which the EOT changes serves as an indication to relative changes in the volume or composition of the cells already present in the microarray.

Thus, the present invention is some embodiments thereof differentiates between static conditions (where the cells cannot multiply) and lethal conditions (where the cells stop to be alive) as inputs for susceptibility test.

The method of the present embodiments can be embodied in many forms. For example, it can be embodied in on a tangible medium such as a computer for performing the method operations. It can be embodied on a computer readable medium, comprising computer readable instructions for carrying out the method operations. In can also be embodied in electronic device having digital computer capabilities arranged to run the computer program on the tangible medium or execute the instruction on a computer readable medium.

At least part of the method of the present embodiments can be can be implemented by a data processing system, e.g., a dedicated circuitry or a general purpose computer, configured for receiving the data and executing at least some of the operations described herein. At least part of the operations can be can be implemented by a cloud-computing facility at a remote location.

Computer programs implementing the method of the present embodiments can commonly be distributed to users on a distribution medium such as, but not limited to, a floppy disk, a CD-ROM, a flash memory device and a portable hard drive. From the distribution medium, the computer programs can be copied to a hard disk or a similar intermediate storage medium. The computer programs can be run by loading the computer instructions either from their distribution medium or their intermediate storage medium into the execution memory of the computer, configuring the computer to act in accordance with the method of this invention. All these operations are well-known to those skilled in the art of computer systems.

A computer software product, according to some embodiments of the present invention can comprise a computer-readable medium in which program instructions are stored, which instructions, when read by a data processor, cause the data processor to receive data pertaining to a diffraction pattern of light diffracted off a diffraction grating having a plurality of compartments containing cells, to calculates a parameter indicative of a refractive index of the cells based on the diffraction pattern, and to determine a time-dependence of a change of the parameter, the time-dependence being indicative of the phenotype of the cells in the biological sample. The data pertaining to a diffraction pattern of light can be in the form of electronic signals generated by a light detector (e.g., CCD camera) of the system used for collecting the optical signals from the grating.

As used herein the term "about" refers to ±10%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof. Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

When reference is made to particular sequence listings, such reference is to be understood to also encompass sequences that substantially correspond to its complementary sequence as including minor sequence variations, resulting from, e.g., sequencing errors, cloning errors, or other alterations resulting in base substitution, base deletion or base addition, provided that the frequency of such variations is less than 1 in 50 nucleotides, alternatively, less than 1 in 100 nucleotides, alternatively, less than 1 in 200 nucleotides, alternatively, less than 1 in 500 nucleotides, alternatively, less than 1 in 1000 nucleotides, alternatively, less than 1 in 5,000 nucleotides, alternatively, less than 1 in 10,000 nucleotides.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non limiting fashion.

Continuous Bacterial Susceptibility Testing by Optical Interferometry Analyses

A device for continuous monitoring of the susceptibility of bacterial cells to extraneous molecules or particles that may possess bactericidal, bacteriostatic, anti-adhesive or anti-motility effect, or any other influence on the ability of the cells to adhere, proliferate or create surface fouling.

Abbreviations:
EOT: Effective Optical Thickness
RPT: Reflective Periodic Topography
MIC: Minimal Inhibitory Concentration
Device and Means
 1. Reflective surface with reflective periodic micron scale topography of photonic interferometry properties, including reflective interferometry spectrum (see FIGS. 1A-F). Said topographies may consist of pores, pillars or groves.
 2. Microfluidic device for the management of bacteria suspensions at the interface of said photonic surfaces (see FIG. 2).

FIGS. 1A-F: A) Top view of a RPT (e.g. 2D pillar periodic array) with proliferating bacterial cells. (B) The light reflected from the pores top and bottom creates a phase delay between the incident and the reflected beams, proportional to the pores depth (L) and refractive index of the medium filling the pores (n). (C) Associated with the pores periodicity, the reflectance phase delay appears as an interference spectrum. (D) Applying Fast Fourier Transform to the raw spectrum, yields the effective optical thickness (EOT) of the porous layer, which depends on the pores average depth and refractive index. (E) Bacterial cells presence within the pores affects the refractive index of the porous layer as function of the relative volume they occupy. (F) The bacteria fraction in the pores is monitored in real time by collecting the effective optical thickness (EOT), as this property is determined by the bacteria relative contribution to the refractive index, n.

Method:

The method includes the continuous or rapid serial monitoring of the light interferometry spectra obtained from a surface with reflective periodic topography (PRT), prior, during and following the controlled introduction of bacterial suspensions to it and/or addition of drugs/substances. Said interferometry spectra is analyzed (for example by fast Fourier transform) to reveal the rate of optical shift, e.g., the time-dependent alterations in the reflected light properties of said PRT, inflicted by the behavior of the cells (for example settling, adhering, migrating or proliferating).

Examples:

The presence and effect of various molecular entities on the cells is analyzed and derived from the deviations in the EOT alteration profile, that testify of the effect said entities has on the cells.

FIG. 14 is a schematic illustration showing experimental and optical principles of a study performed according to some embodiments of the present invention. A SiPA placed in a flow-device having an inlet and an outlet. The SiPA is optionally and preferably posited at the focal point of an optical setup having a lens, a light source (Tungsten lamp, in the present Example), and a light detector (CCD camera, in the present Example) equipped with a spectrometer. Fluid containing bacteria is introduced through the inlet. Light reflected from the top and bottom of the pores is collected by the optical setup. The phase delay between the incident and the reflected light beams is proportional to the depth (L) of the pores, and the refractive index of the medium filling the pores. The presence of bacterial cells in the pores increase the refractive index of the pores. Thus, the phase delay of the reflected light in the presence of the bacteria differs from the phase delay of the reflected light in the absence of the bacteria, so that analysis of the light collected by the optical setup can provide indication regarding the phenotype of the cells.

FIG. 15A shows exemplified spectra obtained before and after the introduction of the bacteria into the pores, and FIG. 15B show FFTs of the exemplified spectra shown in FIG. 15A. The FFT provides the value (2 nL), where L is the average depth of the pores and n is their refractive index. This quantity is also referred to as the Effective Optical Thickness (EOT). The measured shift in the EOT value is a function of the change in the refraction index of the pole: $\Delta EOT/EOT_0 = 2(\Delta n/n_0)L$, where $n_0$ is the refractive index of the pores before the introduction of the bacteria into the pores, $\Delta n$ is the change in the refractive index as a result of the introduction of the cells into the compartments, and $EOT_0$ is the EOT before introducing the cells into the compartments. $\Delta n$ is thus correlated with the pore's volume fraction occupied by bacteria cells.

FIG. 3: The proliferation of *E. coli* on a hybrid PSi array chip plotted in terms of $\Delta EOT$ as function of time. To visualize the cells in the PSi array at discrete time points, some hybrid chips were gently flushed with glutaraldehyde and imaged by using CLSM and SEM. In CLSM images, optical sections are made at the lower pore plane, revealing *E. coli* cells stained red by propidium iodide. In SEM images, *E. coli* cells are contrasted by graphite deposition.

FIG. 4: Real time optical monitoring of *E. coli* bacteria growth arrest upon the introduction of Kanamycin (50 μg/ml), an aminoglycoside bacteriocidal antibiotic drug.

FIG. 5: The dependence of EOT shift on cells' viability and motility. (A) Recorded EOT shift produced by *E. Coli* suspensions with varying bactericidal Iodine concentrations. (B) The rate of EOT shift presented as function of the survived cells and iodine concentration; $R^2=0.98$; (C) The presence of Cranberry extract detachment factor in the suspension affects the rate of EOT shift in a dose dependent manner.

Figure 6B:
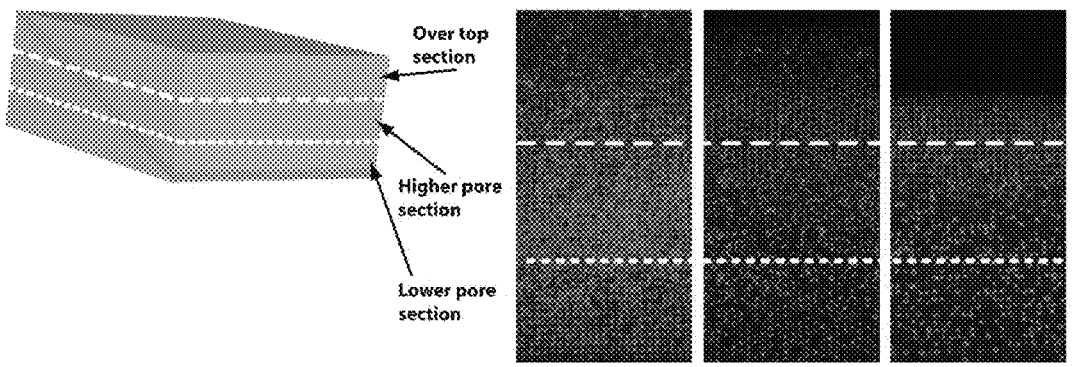
Figure 6D:
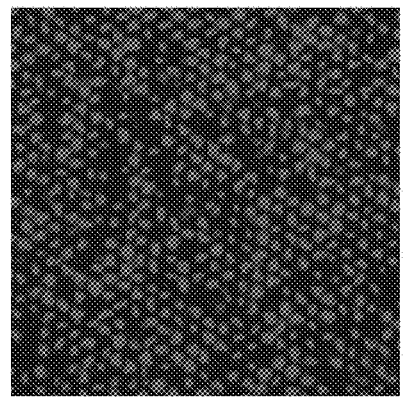
Figure 6E:
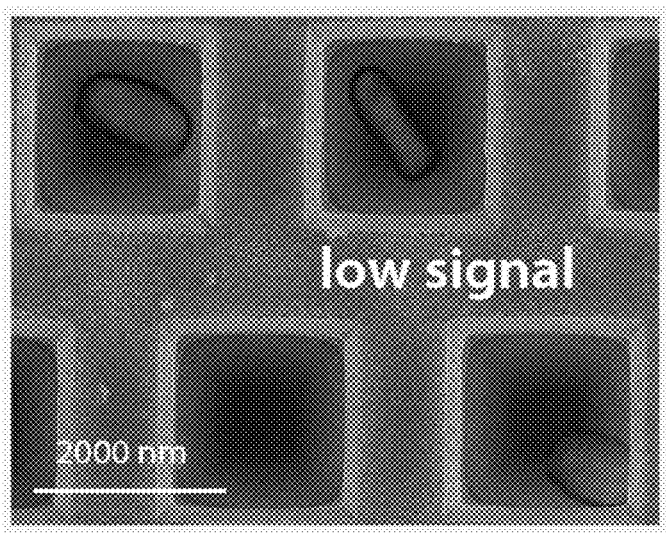
Figure 6E:
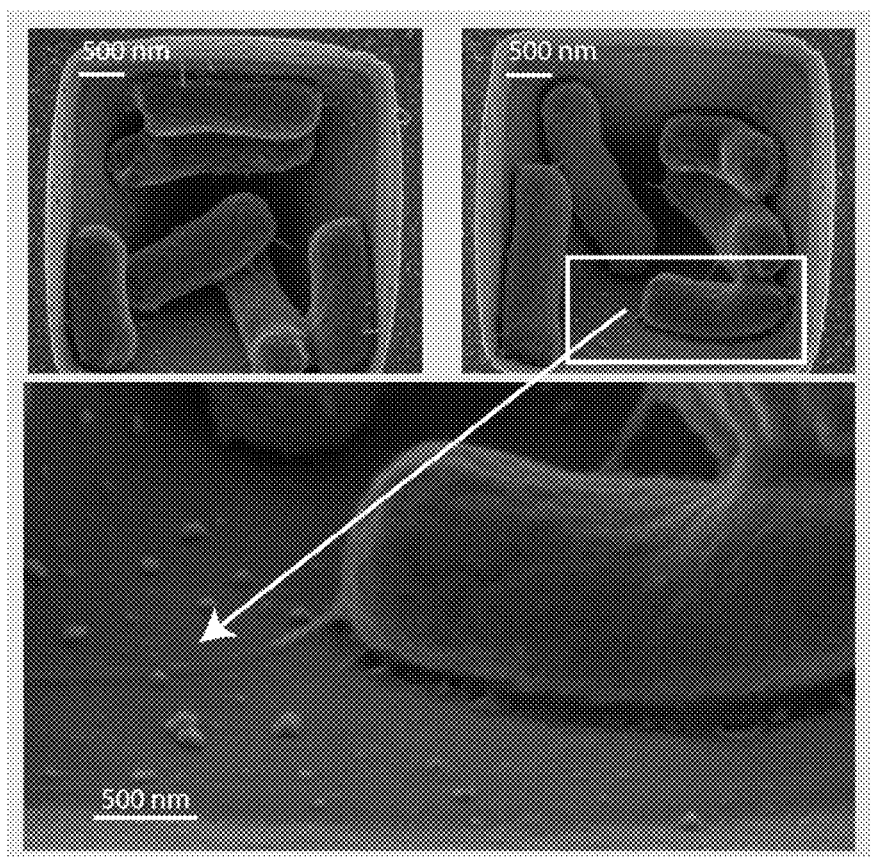

FIGS. 6A to 6F3 demonstrate a reversal of the EOT shift (blue line) upon rinsing the device with clean buffer. FIG. 6A is EOT plot, detailing the increase in EOT during bacteria colonization of the PRT and its partial reversal in response to rinsing the device. The red line in the plot indicate the relative change in signal intensity. FIG. 6B shows microscopic optical cross sections (acquired with CLSM) of the PRT (in Blue) and bacterial cells (in Red) that are reconstructed into a virtual model of the PRT. FIGS. 6C1 to 6C3 show diagonal slicing of the 3D model that reveals the inner 3D structure. FIG. 6C1 represents a device without rinsing, FIG. 6C2 represents a device exposed to short (10 min) rinse, and FIG. 6C3 represents a device exposed to longer (20 min) rinse. FIG. 6D is a CLSM image depicting *E. Coli* cells filing all available SiPA pores, demonstrating that the increase in relative EOT value reach its maximum when no free pore space is left to accommodate additional bacterial cells. FIG. 6E shows a close-up SEM image depicting *E. Coli* cells inside SiPA pores. After establishing a stable EOT baseline, *E. Coli* suspension is introduced into the ¬flow-cell and the cells begin to colonize SiPA pores, producing a relative increase in EOT value. FIGS. 6F1 to 6F3 show SEM images demonstrating cells evading the rinsing to occupy large fraction of the pore's volume and secure to its surface through their extensions and filamentous secretions.

Types of optical kinetic profiles made by bacterial cells on photonic microarrays diffraction grating (e.g., SiPA) include, without limitation, 1. Bacteria cells are seeded into the pores/structures. Full growth media is supplied to the cells until a growth curve is established.
    a. An anti-proliferation drug (bacteriostatic/antibiotics) is added to the media (see FIG. 7) and the correlation of EOT growth curve and drug concentration is analyzed. The MIC (minimal inhibitory concentration) is determined when the EOT shift becomes null.
    b. If the drug is later remove from the media (see FIG. 8), the cell growth may resume, if the drug effect is reversible.
    c. If the drug is bactericidal or its bacteriostatic effect is irreversible, then the EOT curve will retract as dead cells disintegrate and exit the pores (see FIG. 8).
    d. If the growth media if deficient with critical nutrient or factor, then EOT growth curve will decline in relation to the deficiency (see FIG. 9).
2. Bacteria suspension is introduced to the photonic microarrays diffraction grating under constant flow conditions, in salt buffer solution.
    a. If the suspension contains an anti-attachment drug/factor that will affect pore/structure colonization, then correlation of EOT curve and drug concentration can be analyzed (see FIG. 10).

b. Once a stable EOT curve is established, the bacteria suspension is replaced with clean buffer to challenge the bacteria adhesion. If cells are rinsed out of the pores, EOT plot will retract (see FIG. 11).

FIGS. 12A and 12B are graph demonstrating that SiPA colonization depends on its surface functionality. FIG. 12A shows that coating SiPA with Wheat-germ agglutinin (WGA) improves *E. Coli* colonization 5 times over neat SiO2 or albumin. The incorporation of WGA ligand (NAG) in the suspension, completely eliminate this effect. FIG. 12B shows the rate of EOT shift given for the above silicon surface functions.

FIGS. 13A and 13B are graphs that demonstrate that SiPA Colonization rate is a function of cell concentration. FIG. 13A shows concentration of *E. Coli* in suspension in terms of available Cell per Pore. FIG. 13B shows that the rate of EOT shift is linearly correlated to the cell number.

FIGS. 16A-C and 17 show antibiotic susceptibility testing using the photonic microarrays diffraction grating of the present embodiments. Three different antibiotics were chosen for the preliminary AST experiments: Ciprofloxacin, Ceftriaxone Sodium, and Trimethoprim. These antibiotics were selected due to their diverse antibacterial mechanisms in addition to their prevalence in current clinical ASTs. Ciprofloxacin is a fluoroquinolone, which inhibits DNA gyrase thus preventing cell replication and exhibit a bacteriostatic effect. Ceftriaxone Sodium is a β-lactam antibiotic, third generation cephalosporin, which disrupts the synthesis of the cell wall, eventually causing cell lysis as the bacterium begins to divide, ideally exhibiting a bactericidal effect. Trimethoprim interferes with folic acid synthesis and prevents DNA synthesis, thus exhibit a bacteriostatic effect. Standard microdilution broth testing was performed to ascertain the Minimal Inhibitory Concentration (MIC) of each antibiotic agent. Results of testing Ciprofloxacin, Ceftriaxone Sodium, and Trimethoprim at various concentrations on the proliferation of *E. coli* are depicted in FIGS. 16A-C, where the antibiotic agent were introduced at increasing concentrations, starting from below its known MIC value and above it. The MIC of Ceftriaxone Sodium (CRO) is observed to be between 0.005-0.05 µg/mL. The MIC of Ciprofloxacin (CIP) is observed to be between 0.005-0.05 µg/mL. The MIC of Trimethoprim (TMP) is observed to be between 5-50 µg/mL.

Thus, these results demonstrate the ability of the photonic microarrays diffraction grating of the present embodiments to respond correctly to the MIC of an antibiotic agent, retrieved from the bacteria growth related EOT shift. Cross-analysis of the effect of the three antibiotics at the same concentration is presented in FIGS. 13A-B. The present studies prove that 2 hours after the *E. coli* are exposed to relevant antibiotic MIC value, the bacteria growth arrest can be reliably detected.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A method of determining a phenotype of cells in a biological sample, the method comprising:
   (a) incubating for a predetermined time said biological sample comprising said cells on a diffraction grating containing an ordered array of compartments having lateral dimensions such that said cells can fit therein;
   (b) continuously detecting over said predetermined time illumination diffracted from said diffraction grating comprising said cells upon illumination of said surface with illumination over a range of wavelengths and generating therefrom an output spectrum signal;
   (c) determining from said output spectrum signal a time-dependence change of an effective optical thickness (EOT) of said compartments incubated with said biological sample, and
   (d) determining said phenotype of said cells in said biological sample based on said time-dependence.

2. The method of claim 1, wherein said biological sample comprises a test agent.

3. The method of claim 2, further comprising performing the method in an absence of said test agent.

4. The method of claim 3, wherein said change of said parameter is a change of a value said parameter in said presence of said test agent relative to a value of a value said parameter in said absence of said test agent.

5. The method of claim 4, further comprising generating an output indicative of an effect of said test agent on the phenotype of the cells in said biological sample, based on said time-dependence.

6. The method of claim 4, wherein when said time-dependence is indicative of a decrease in an effective optical thickness (EOT), said test agent is a cytocidal agent.

7. The method of claim 4, wherein when said time-dependence is substantially flat said test agent is a cytostatic agent.

8. The method of claim 1, wherein said diffraction grating comprises a test agent adhered to said compartments.

9. The method of claim 1, wherein said phenotype is selected from the group consisting of viability, motility, biofilm production, colonization, protein production and lipid production.

10. The method of claim 1, wherein said cells are incubated with said diffraction grating so as to fill said compartments.

11. The method of claim 1, wherein said cells are bacteria.

12. The method of claim 1, wherein said cells are eukaryotic cells.

13. The method of claim 1, wherein said cells are cancer cells.

14. The method of claim 1, wherein said biological sample comprises a test agent which is selected from the group consisting of an antibiotic, a chemotherapy, a radio-isotope, a herbicide and a fungicide.

15. A method of determining a phenotype of cells, the method comprising:
   (a) placing said cells in a plurality of compartments of a diffraction grating;
   (b) diffracting a polychromatic light beam by said diffraction grating;
   (c) calculating a parameter indicative of a refractive index of said cells based on a diffraction pattern received from said diffraction grating;

(d) determining a time-dependence of a change of said parameter, and (e) determining said phenotype of said cells in said biological sample based on said time-dependence.

16. The method of claim 15, wherein said parameter comprises effective optical thickness (EOT) of said compartments, and said change is with respect to a value of said EOT in the absence of said cells.

17. The method of claim 15, wherein said diffracting comprises effecting reflective diffraction.

18. The method of claim 15, wherein said diffracting comprises effecting transmissive diffraction.

19. The method of claim 15, wherein said polychromatic light beam is generally white.

20. A computer software product, comprising a non-transitory computer-readable medium in which program instructions are stored, which instructions, when read by a data processor, cause the data processor to receive data pertaining to a diffraction pattern of light diffracted off a diffraction grating having a plurality of compartments containing cells, to calculate a parameter indicative of a refractive index of said cells based on said diffraction pattern, to determine a time-dependence of a change of said parameter, to accesses a non-transitory computer readable medium storing a database of reference time-dependences, to search said database for a database time-dependence that matches said determined time-dependence, and to generate on a display an output indicative of said phenotype of said cells in said biological sample based on said database time-dependence.

* * * * *